United States Patent
Deng et al.

(10) Patent No.: US 11,524,000 B2
(45) Date of Patent: Dec. 13, 2022

(54) TARGETING MCL-1 TO ENHANCE DNA REPLICATION STRESS SENSITIVITY FOR CANCER THERAPY

(71) Applicant: Emory University, Atlanta, GA (US)

(72) Inventors: Xingming Deng, Atlanta, GA (US); Guo Chen, Atlanta, GA (US); Abu Syed Md Anisuzzaman, Atlanta, GA (US)

(73) Assignee: Emory University, Atlanta, GA (US)

( * ) Notice: Subject to any disclaimer, the term of this patent is extended or adjusted under 35 U.S.C. 154(b) by 169 days.

(21) Appl. No.: 16/759,199

(22) PCT Filed: Oct. 23, 2018

(86) PCT No.: PCT/US2018/057114
§ 371 (c)(1),
(2) Date: Apr. 24, 2020

(87) PCT Pub. No.: WO2019/084010
PCT Pub. Date: May 2, 2019

(65) Prior Publication Data
US 2020/0316011 A1     Oct. 8, 2020

Related U.S. Application Data

(60) Provisional application No. 62/577,565, filed on Oct. 26, 2017.

(51) Int. Cl.
*A61K 31/343* (2006.01)
*A61P 35/00* (2006.01)
*A61K 31/15* (2006.01)
*A61K 31/17* (2006.01)
*A61K 31/502* (2006.01)
*A61K 31/517* (2006.01)
*A61K 45/06* (2006.01)

(52) U.S. Cl.
CPC ............ *A61K 31/343* (2013.01); *A61K 31/15* (2013.01); *A61K 31/17* (2013.01); *A61K 31/502* (2013.01); *A61K 31/517* (2013.01); *A61P 35/00* (2018.01); *A61K 45/06* (2013.01)

(58) Field of Classification Search
CPC .................................................... A61K 31/343
USPC ....................................................... 514/248
See application file for complete search history.

(56) References Cited

U.S. PATENT DOCUMENTS

2015/0164933 A1   6/2015   Chiao
2017/0151284 A1   6/2017   Dalemans

FOREIGN PATENT DOCUMENTS

WO   2014139014   9/2014

OTHER PUBLICATIONS

Belmar et al. Small molecule Mcl-1 inhibitors for the treatment of cancer, Pharmacol Ther. 2015, 145: 76-84.
Chen et al. Mcl-1 dictates DNA double-strand break repair pathway choice, AACR 107th Annual Meeting 2016, Abst 2757.
Chen et al., Targeting Mcl-1 enhances DNA replication stress sensitivity to cancer therapy, J Clin Invest. 2018;128(1):500-516.
Chiu et al. Novel Quinazoline HMJ-30 Induces U-2 OS Human Osteogenic Sarcoma Cell Apoptosis through Induction of Oxidative Stress and Up-Regulation of ATM/p53 Signaling Pathway, J Orthop Res 29:1448-1456, 2011.
Lallo et al. The Combination of the PARP Inhibitor Olaparib and the WEE1 Inhibitor AZD1775 as a New Therapeutic Option for Small Cell Lung Cancer, Clin Cancer Res, 2018, 1-12.
Matoo et al. MCL-1 Depletion Impairs DNA Double-Strand Break Repair and Reinitiation of Stalled DNA Replication Forks, Mol Cell Biol, 2017, 37:e00535-16.
Pubchem, NSC320223, 2-(2-chlorophenyl)-3-[(E)-(3-ethoxy-2-hydroxyphenyl)methylideneamino]quinazolin-4-one, 2019, available at https://pubchem.ncbi.nlm.nih.gov/compound/135452546.
Rhee et al. Synthesis and Evaluation of Antimicrobial-antitumor Activities of Methylthiosemi-carbazones and Thiocarbohydrazones, Journal of the Pharmaceutical Society of Korea, 1972, 16:162-175.
Krishan et al., Synthesis, antiviral and cytotoxic investigation of 2-phenyl-3-substituted quinazolin-4(3H)-ones, European Review for Medical and Pharmacological Sciences, 2011, 15: 673-681.

*Primary Examiner* — Taofiq A Solola
(74) *Attorney, Agent, or Firm* — Emory Patent Group

(57) ABSTRACT

This disclosure relates to inhibitors of Mcl-1 stimulated homologous recombination (HR) DNA repair and uses for treating cancer. In certain embodiments, this disclosure relates to methods of treating cancer comprising administering an inhibitor of Mcl-1 in combination with other anti-cancer agents, e.g., that induce DNA replication stress. In certain embodiments, this disclosure relates to methods of treating cancer comprising administering compounds disclosed herein in combination with hydroxyurea, olaparib, or combinations thereof.

7 Claims, 14 Drawing Sheets

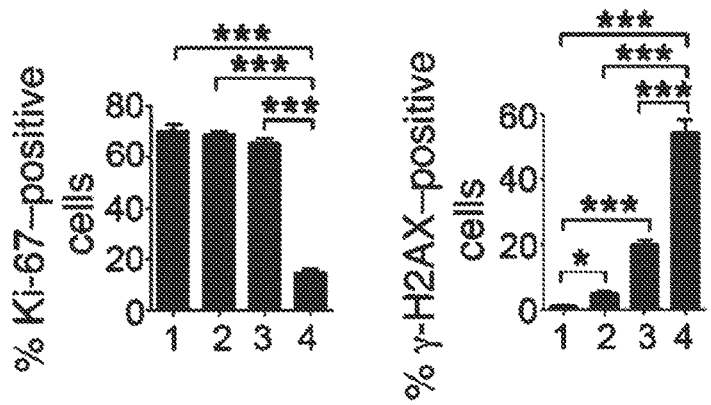
FIG. 5B
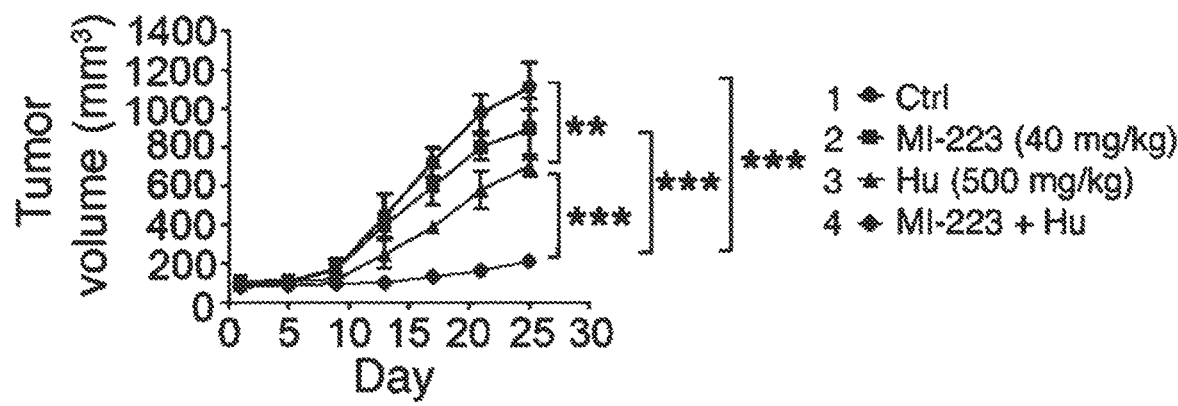
FIG. 5C
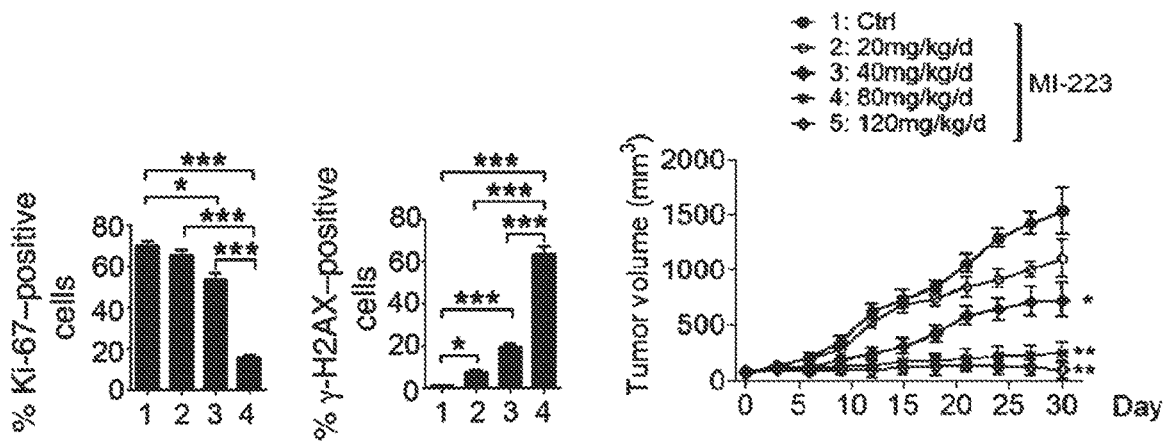
FIG. 5D
FIG. 6

TARGETING MCL-1 TO ENHANCE DNA REPLICATION STRESS SENSITIVITY FOR CANCER THERAPY

CROSS-REFERENCE TO RELATED APPLICATIONS

This application is the National Stage of International Application No. PCT/US2018/057114 filed Oct. 23, 2018, which claims the benefit of U.S. Provisional Application No. 62/577,565 filed Oct. 26, 2017. The entirety of each of these applications is hereby incorporated by reference for all purposes.

STATEMENT REGARDING FEDERALLY SPONSORED RESEARCH OR DEVELOPMENT

This invention was made with government support under R01CA193828, R01CA136534, and R01CA200905 awarded by the National Institutes of Health. The government has certain rights in the invention.

BACKGROUND

Lung cancer is often classified as non-small cell lung cancer or small cell lung cancer. Non-small cell lung cancer accounts for vast majority of lung cancers. The standard of care for advanced small cell lung cancer and non-small cell lung cancer includes radiation and chemotherapy, e.g., cisplatin and etoposide. Lung cancer is a global health problem. For example, in the United States, more patients die from lung cancer alone than prostate, breast and colon cancers combined. Thus, there is a need to identify improved therapies.

DNA double-strand breaks (DSBs) can be induced by radiation and chemotherapy drugs. DSB repair pathway mechanisms impact cancer progression as inappropriate repair of DSBs may result in the propagation of deleterious mutations and genomic instability. Myeloid cell leukemia sequence 1 (Mcl-1) is an anti-apoptotic Bcl-2 family member that is sometimes overexpressed in tumors. In addition to its cell survival function, Mcl-1 has been demonstrated to localize to sites of DNA damage. Mattoo et al. report MCL-1 depletion impairs DNA double-strand break repair and re-initiation of stalled DNA replication forks. Mol Cell Biol. 2017, 37(3):e00535-16.

References cited herein are not an admission of prior art.

SUMMARY

This disclosure relates to inhibitors of Mcl-1 stimulated homologous recombination (HR) DNA repair and uses for treating cancer. In certain embodiments, this disclosure relates to methods of treating cancer comprising administering an inhibitor of Mcl-1 in combination with other anti-cancer agents, e.g., that induce DNA replication stress. In certain embodiments, this disclosure relates to methods of treating cancer comprising administering compounds disclosed herein in combination with hydroxyurea, olaparib, or combinations thereof.

In certain embodiments, this disclosure relates to methods of treating cancer comprising administering an effective amount of a compound that inhibits Mcl-1-stimulated homologous recombination DNA repair to a subject in need thereof. In certain embodiments, the compound that inhibits Mcl-1-stimulated homologous recombination DNA repair specifically binds with Mcl-1 BH1 domain (aa256-265).

In certain embodiments, the compound is (MI-223) 2-(2-chlorophenyl)-3-(((5-ethoxy-6-oxocyclohexa-2,4-dien-1-ylidene)methyl)amino)quinazolin-4(3H)-one, salts, or derivatives thereof.

In certain embodiments, the compound is (MI-361) N'-(2-nitrobenzylidene)-2-(2-nitrobenzylidene)hydrazine-1-carbothiohydrazide, salts, or derivatives thereof.

In certain embodiments, the compound is (MI-647) 6,6'-((phthalazine-1,4-diylbis(hydrazine-2,1-diyl))bis(methanylylidene))bis(cyclohexa-2,4-dien-1-one), salts, or derivatives thereof.

In certain embodiments, the compound is (MI-985) N-(2,5-dimethylphenyl)-4-(naphthalen-2-yl)-2,4-dioxo-3-(3-oxo-1,3-dihydroisobenzofuran-1-yl)butanamide, salts, or derivatives thereof.

In certain embodiments, compound is administered in combination with hydroxyurea or olaparib. In certain embodiments, the compound is administered in combination with another anticancer agent.

In certain embodiments, the compound is administered in combination with bevacizumab, trastuzumab, imatinib, lenalidomide, pemetrexed, bortezomib, cetuximab, leuprorelin, abiraterone, alemtuzumab, nivolumab, pembrolizumab, pidilizumab, atezolizumab, avelumab, cyclophosphamide, methotrexate, 5-fluorouracil, doxorubicin, mustine, vincristine, procarbazine, prednisolone, bleomycin, vinblastine, dacarbazine, etoposide, cisplatin, epirubicin, cisplatin, capecitabine, folinic acid, oxaliplatin, or combinations thereof.

In certain embodiments, the combination is CMF, AC, MOPP, ABVD, CHOP, RCHOP, BEP, MVAC, FOLFOX, CAV, or ECF.

In certain embodiments, the subject is a human diagnosed with cancer.

In certain embodiments, the cancer is lung cancer, Hodgkin's or non-Hodgkin's lymphoma, chronic lymphoid leukemia, colorectal cancer, breast cancer, esophagus cancer, stomach cancer, leukemia, GI cancer, multiple myeloma, mantle cell lymphoma, colon cancer, brain cancer, head and neck cancer, prostate cancer, or ovarian cancer.

In certain embodiments, this disclosure relates to pharmaceutical compositions comprising a compound as reported herein and a pharmaceutically acceptable excipient. In certain embodiments, pharmaceutical composition contains a compound disclosed herein and another anti-cancer agent.

In certain embodiments, the disclosure relates to a compound disclosed herein, or pharmaceutical composition comprising the same, for use the treatment or prevention of cancer. In certain embodiments, the disclosure relates to uses of compounds disclosed herein, or pharmaceutical composition comprising the same, for the treatment or prevention of cancer. In certain embodiments, the disclosure relates to uses of compounds disclosed herein in the production of a medicament for the treatment or prevention of cancer.

Figure 1A:
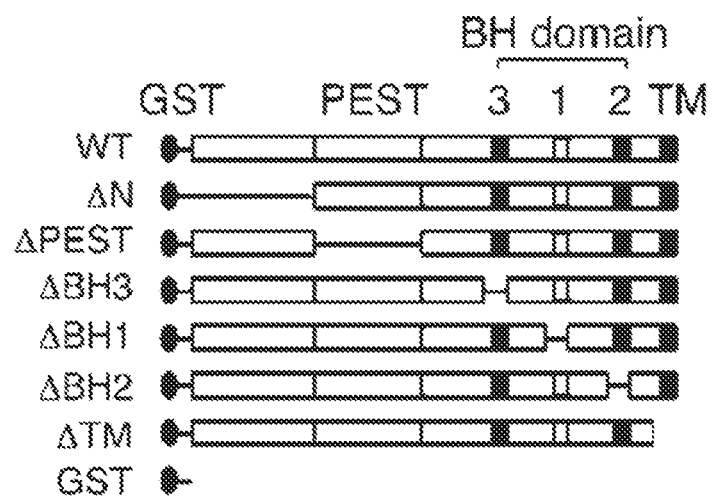
FIG. 1A shows a schematic representation of various Mcl-1 deletion mutants.
Figure 1B:
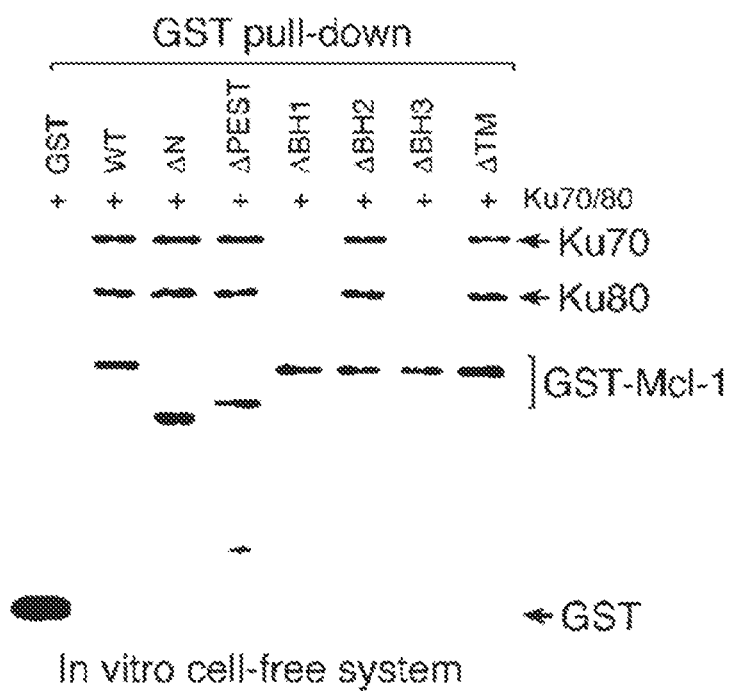
FIG. 1B shows data where GST beads coated with purified recombinant GST-tagged WT or individual Mcl-1 deletion mutants were incubated with recombinant Ku70/Ku80 heterodimer. Mcl-1-associated Ku70 or Ku80 and GST-Mcl-1 were analyzed by Western blot.
Figure 1C:
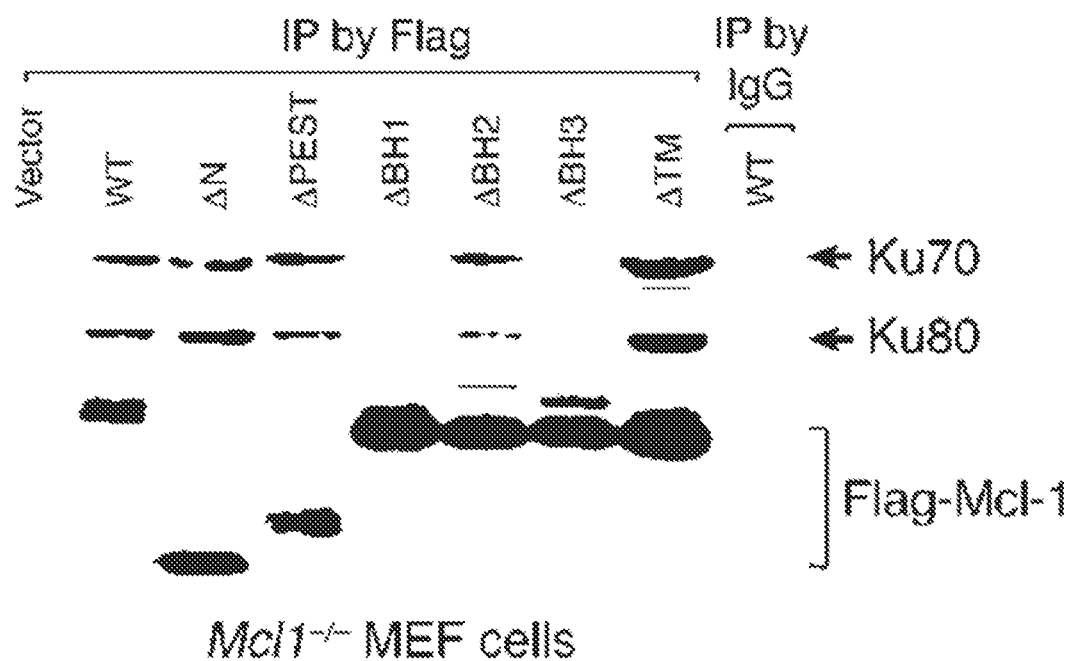
FIG. 1C shows data where Mcl1−/− MEFs were transfected with FLAG-tagged Mcl-1 WT or individual Mcl-1 deletion mutants using Amaxa electroporation System™. Co-IP experiments were performed using anti-FLAG M2 beads, followed by Western blot analysis of Ku70, Ku80, and FLAG-Mcl-1.
Figure 1D:
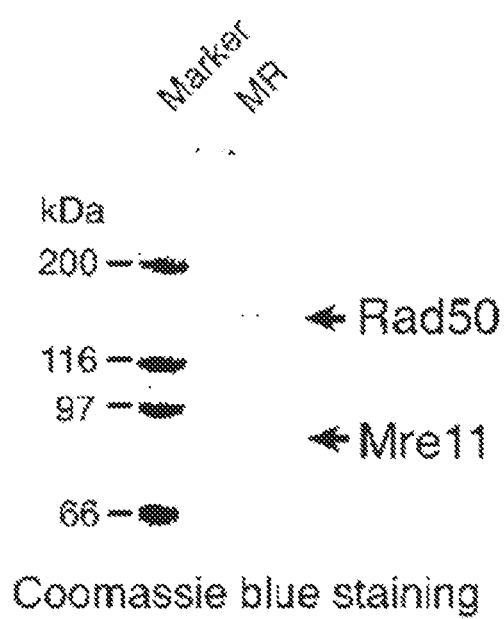

FIG. 1D shows data where Mre11-Rad50 (MR) complex was expressed in Sf9 insect cells and purified using an anti-FLAG M2 affinity column.

Figure 1E:
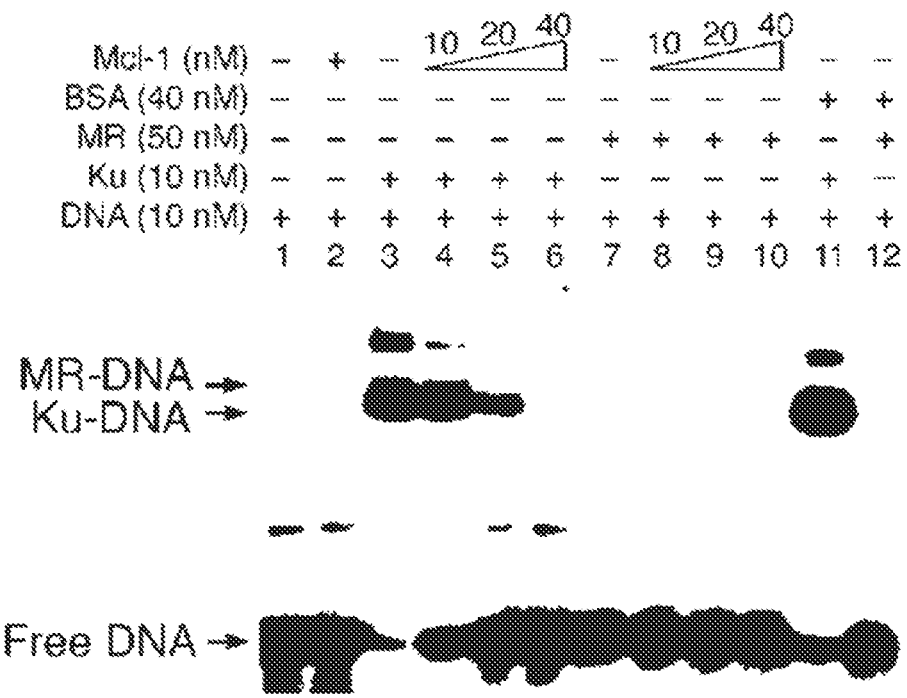

FIG. 1E shows data where the 5'-end-labeled overhang DNA was incubated with Ku or MR complex in the absence or presence of increasing concentrations of Mcl-1.

Figure 1F:
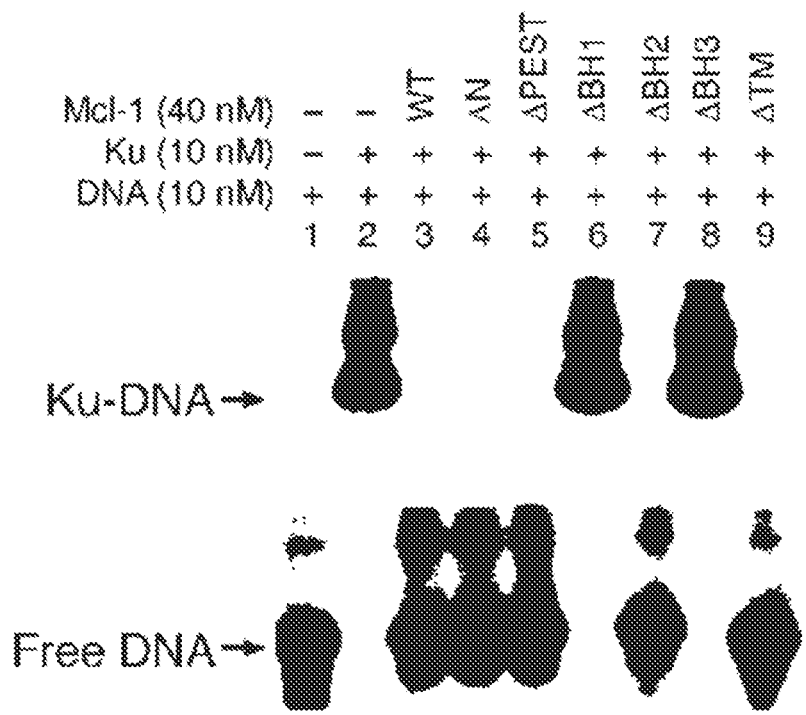

FIG. 1F shows data on individual Mcl-1 deletion mutant proteins.

Figure 2A:
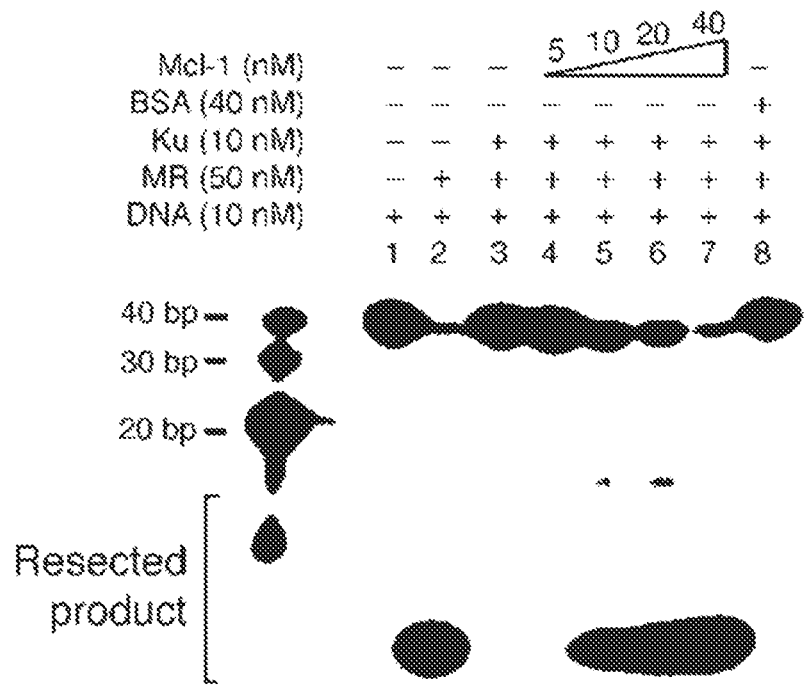
Figure 2B:
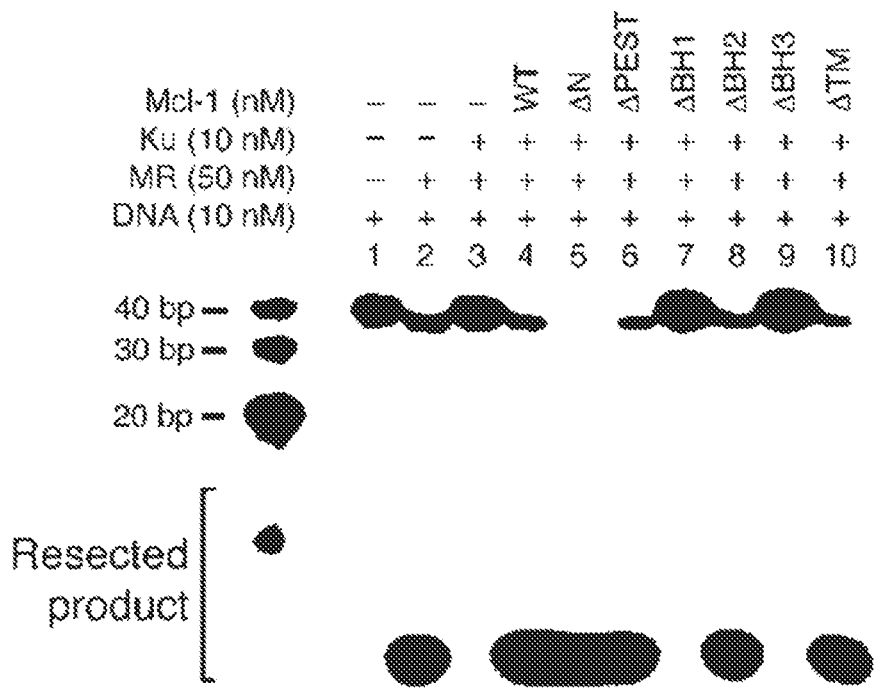

FIG. 2A shows data where 5'-end-labeled forked DNA substrate was incubated with MR complex in the absence or presence of Ku and/or increasing concentrations of WT Mcl-1 protein FIG. 2B shows data using an individual Mcl-1 deletion mutant protein.

Figure 2C:
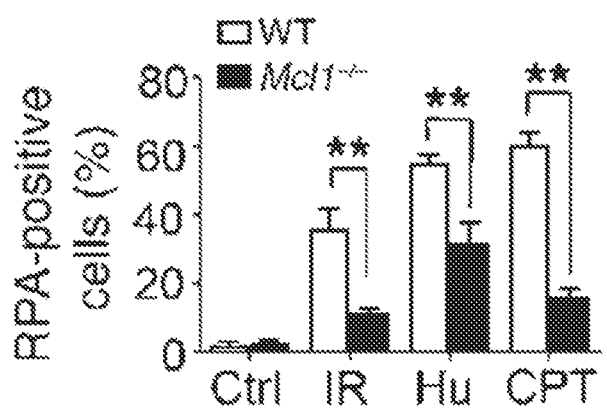

FIG. 2C shows data where MEF WT and MEF Mcl1−/− cells were treated with Hu (0.2 mM) for 24 hours or CPT (1 μM) for 1 hour or exposed to IR (5 Gy), followed by immunostaining with anti-RPA2 antibody.

Figure 2D:
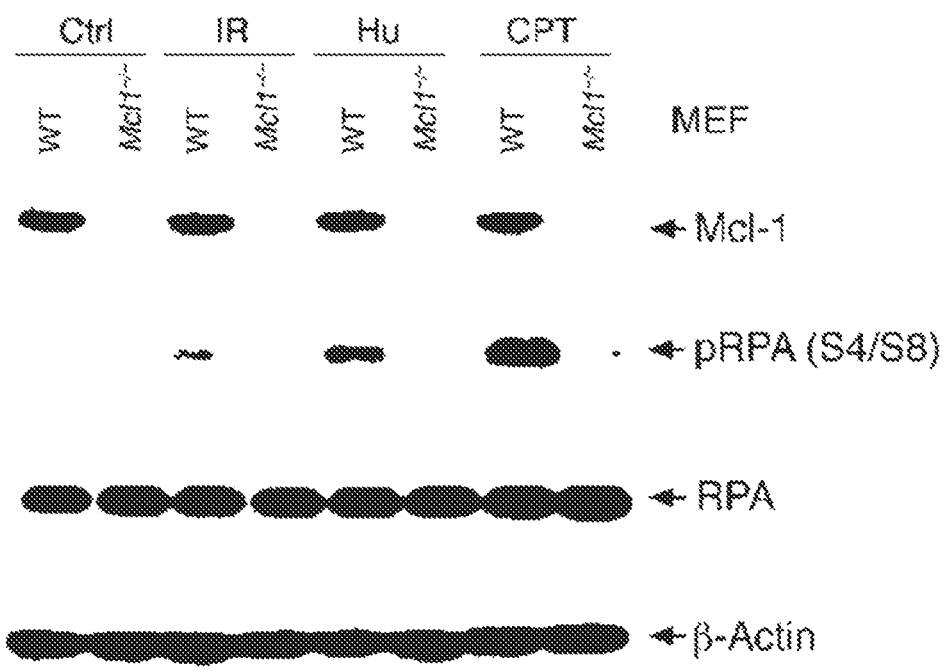

FIG. 2D shows data where RPA2 phosphorylation at Ser4 and Ser8 was analyzed by Western blot using the S4/S8 dual-site phosphor-specific RPA2 antibody following exposure of MEF WT or MEF Mcl1−/− cells to IR (5 Gy), Hu (0.2 mM) for 24 hours, or CPT (1 μM) for 1 hour.

Figure 3A:
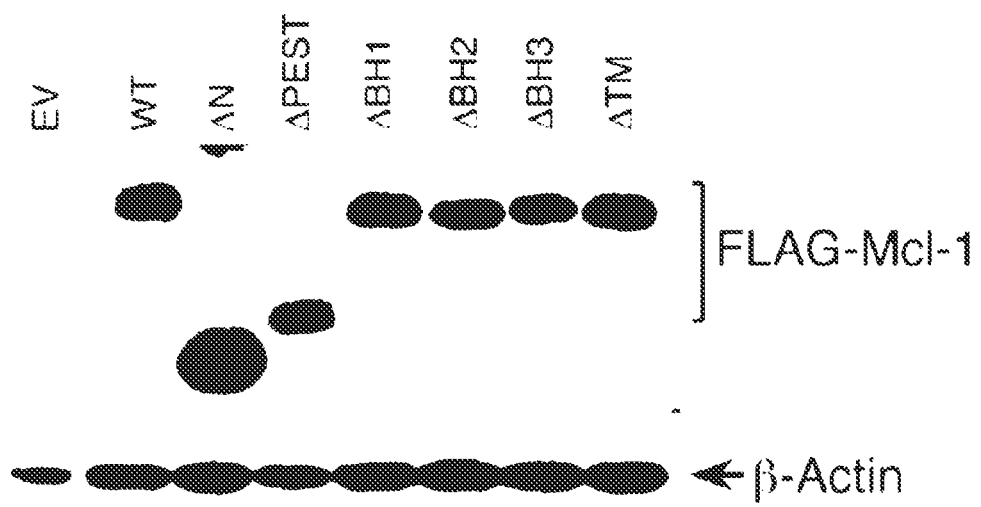

FIG. 3A shows data where FLAG-tagged WT or individual Mcl-1 deletion mutants were transfected into Mcl1−/− MEFs. Mcl-1 expression was analyzed by Western blot using FLAG antibody.

Figure 3C:
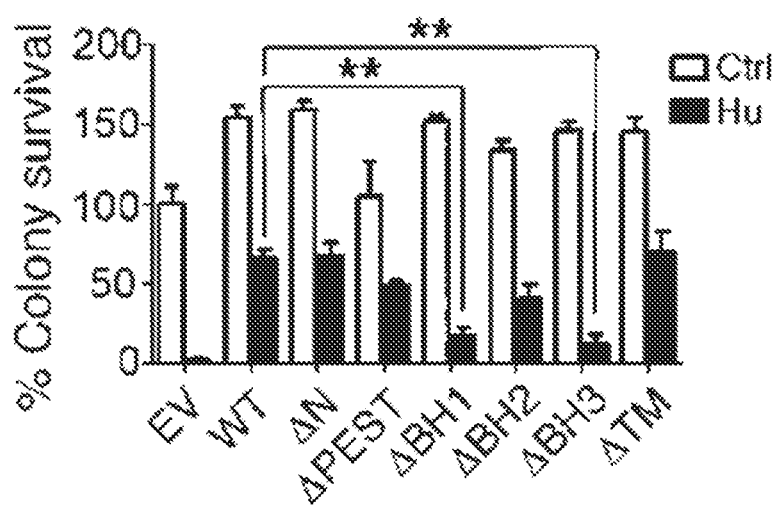
Figure 3B:
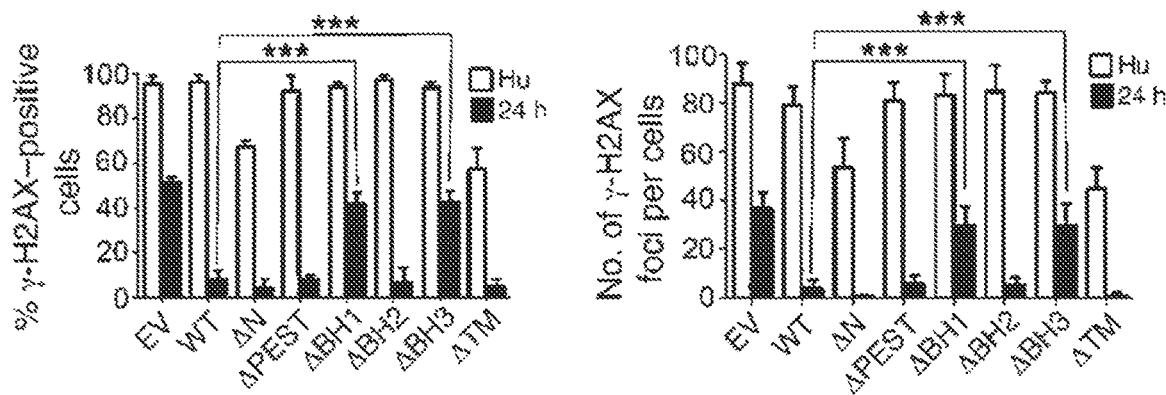

FIG. 3B shows data where Mcl1−/− MEFs expressing exogenous WT or individual Mcl-1 deletion mutants were treated with 0.2 mM Hu for 24 hours. After washing, cells were cultured in normal medium for another 24 hours. DSBs were analyzed by immunofluorescence using γ-H2AX antibody. The percentage of γ-H2AX-positive cells (left panel) and the number of γ-H2AX foci per cell (right panel) were determined by counting of at least 100 cells from each sample.

FIG. 3C shows data where Mcl1−/− MEFs expressing exogenous WT or individual Mcl-1 deletion mutants were treated with 0.2 mM Hu for 24 hours. After washing, cells were cultured in normal medium, followed by colony formation analysis. EV, empty vector.

Figure 4A:
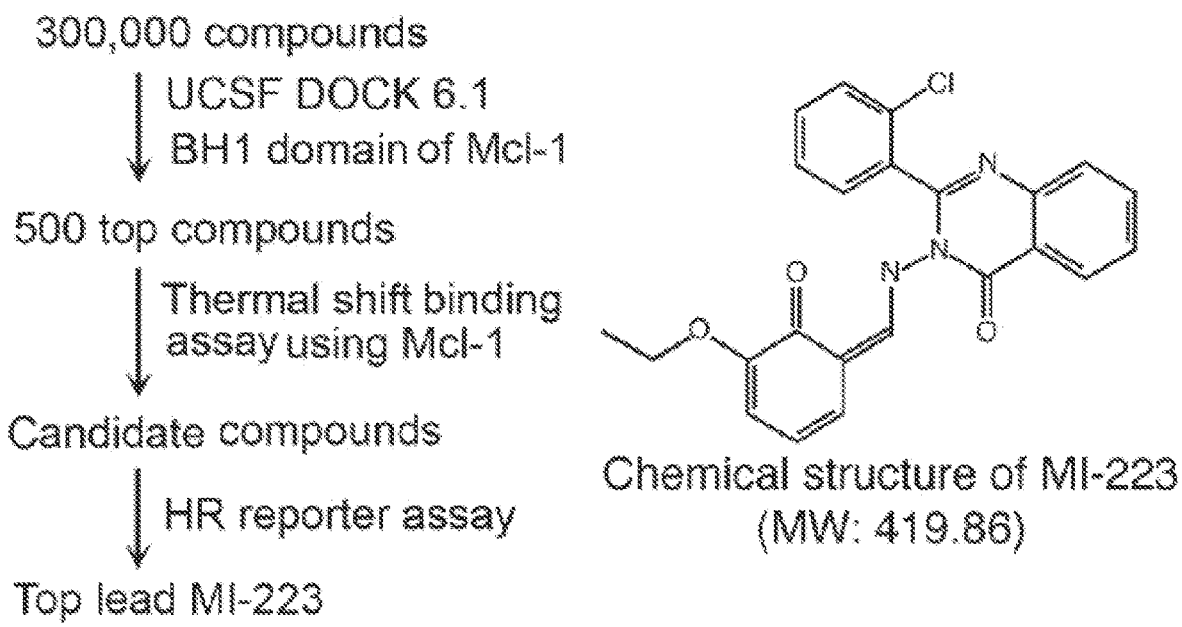

FIG. 4A shows a Schematic illustration of screening strategies used to identify the lead compound Mcl-1 inhibitor MI-223 and its chemical structure.

Figure 4B:
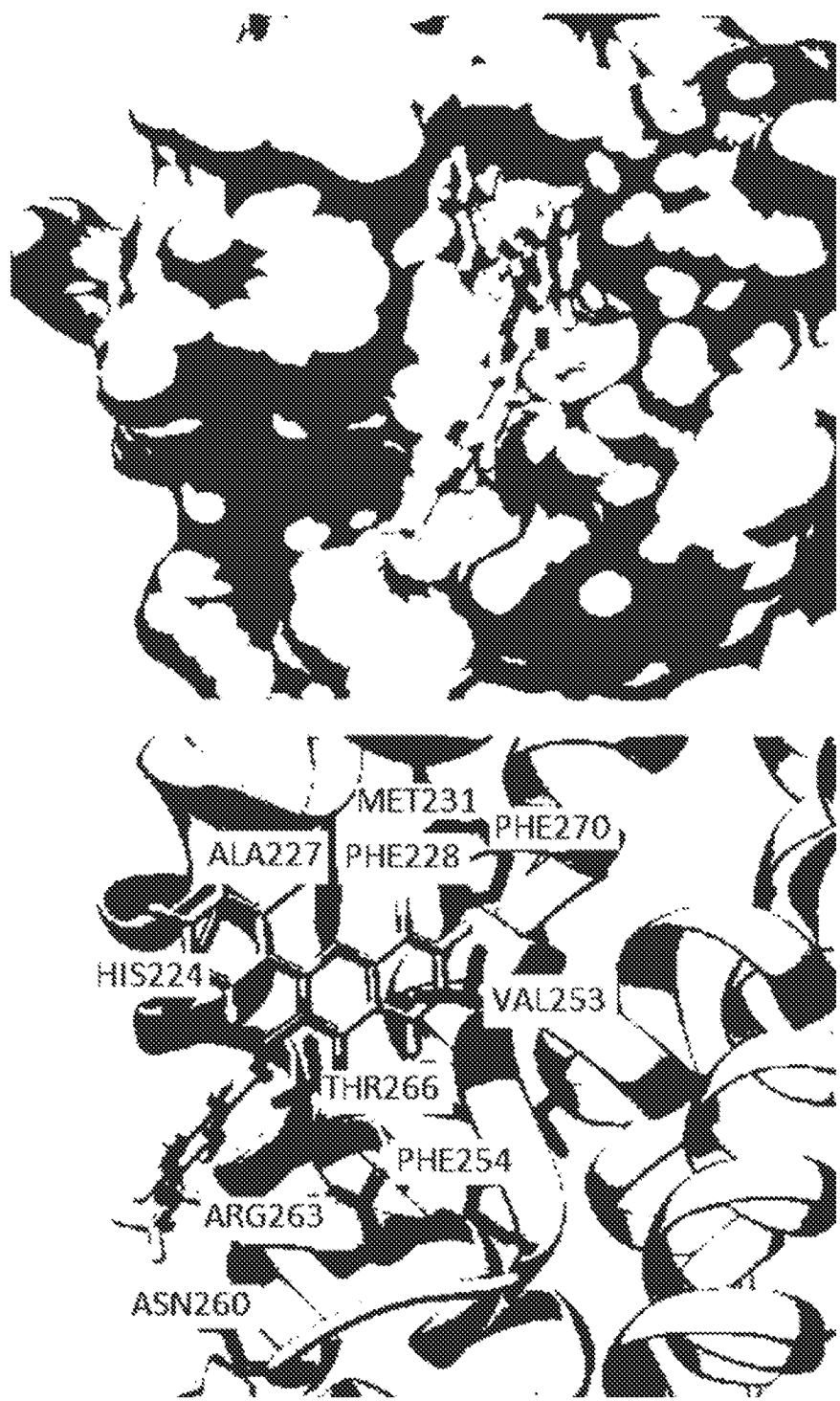

FIG. 4B shows structural modeling of MI-223 in the BH1 domain, binding pocket of Mcl-1 protein.

Figure 4C:
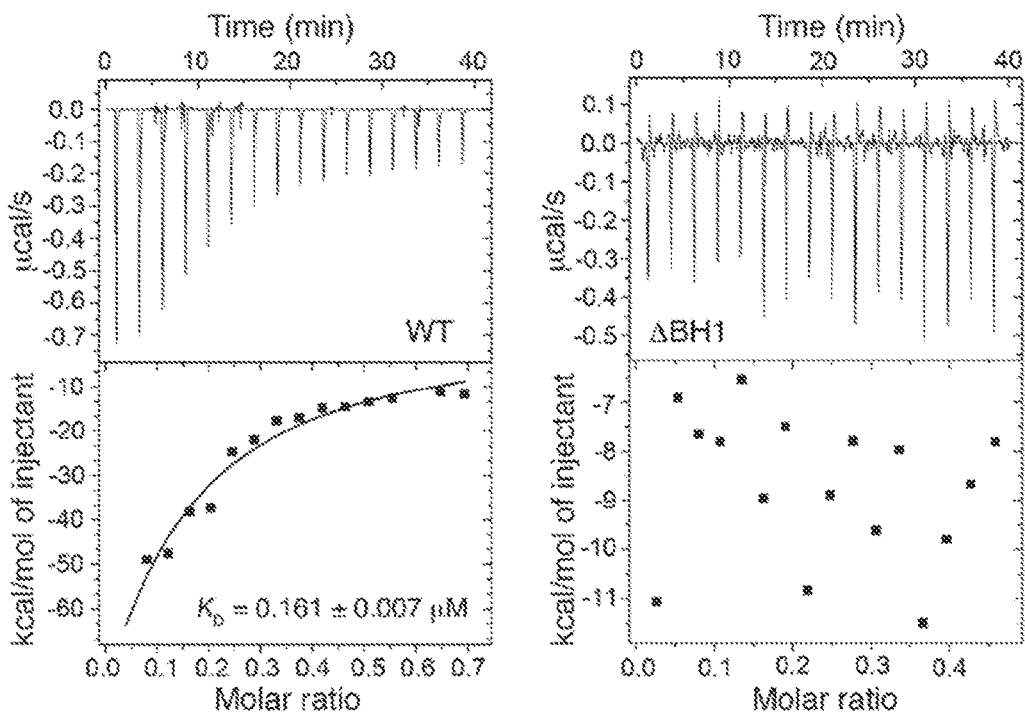
Figure 4D:
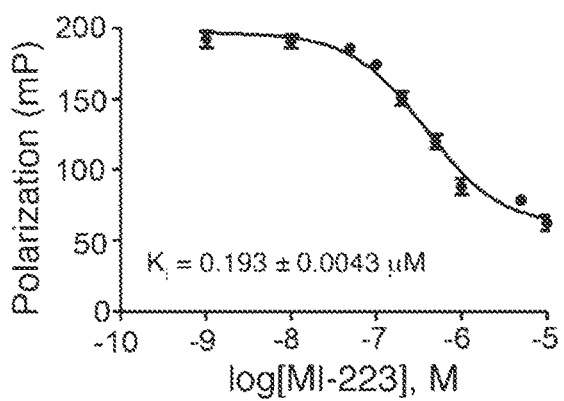

FIG. 4C shows data on the binding affinity of MI-223 with WT Mcl-1 or ΔBH1 Mcl-1 deletion mutant protein was examined by isothermal titration calorimetry assay. The binding constant (KD) value was determined by fitting of the titration curve to a 1-site binding mode FIG. 4D shows data where a fluorescence polarization assay was performed to measure the inhibitory constant (KI) value using purified Mcl-1 protein, MI-223, and fluorescence-labeled PUMA BH3 peptide.

Figure 4E:
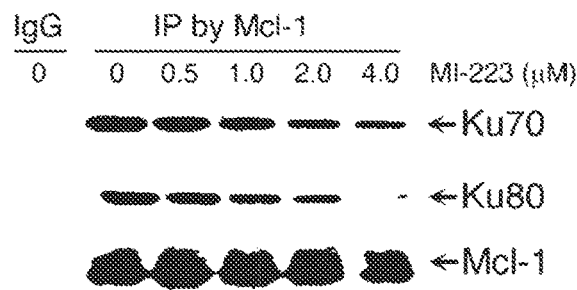

FIG. 4E shows data where H1299 cells were treated with increasing concentrations of MI-223 for 24 hours, followed by co-IP using Mcl-1 antibody.

Figure 4F:
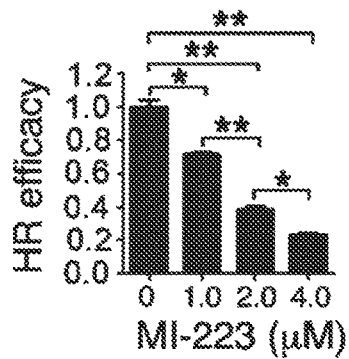

FIG. 4F shows data where HR repair efficiency was measured in H1299 DR-GFP cells in the absence or presence of increasing concentrations of MI-223.

Figure 4G:
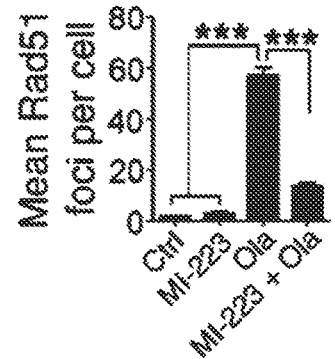

FIG. 4G shows data where H1299 cells were treated with olaparib (Ola, 20 μM), MI-223 (4 μM), or the combination for 24 hours, followed by immunostaining with Rad51 antibody. Rad51 foci were quantified by counting of at least 100 cells from each sample.

Figure 4H:
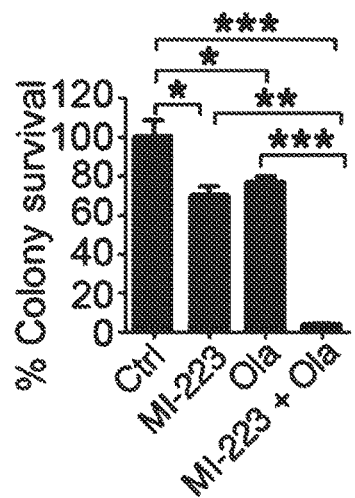

FIG. 4H shows data where H1299 cells were treated with Ola (2 μM), MI-223 (2 μM), or the combination, followed by colony formation assay.

Figure 5A:
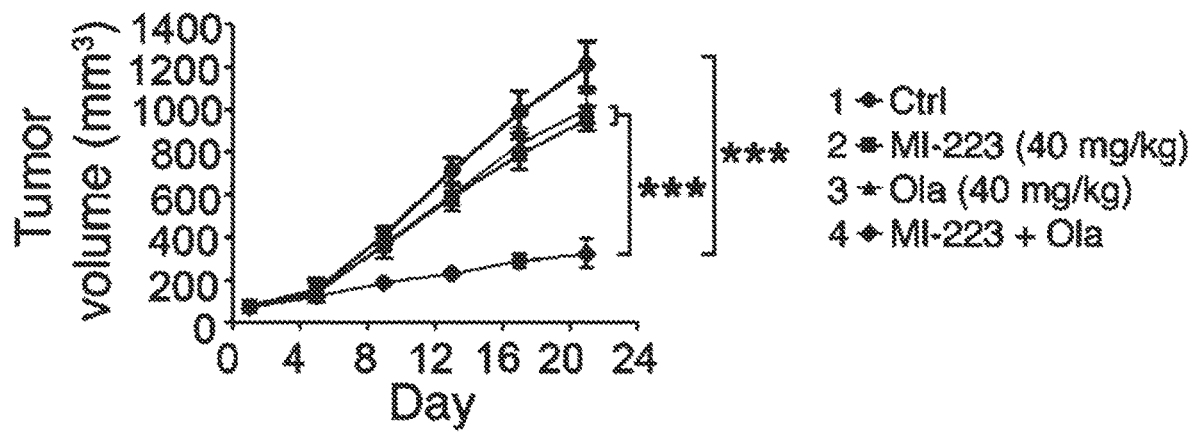

FIG. 5A shows data where nu/Nu nude mice with H1299 lung cancer xenografts were treated with MI-223 (40 mg/kg), olaparib (Ola, 40 mg/kg), or the combination for 3 weeks. Tumor volume was measured once every 4 days. After 21 days, mice were sacrificed and tumors were removed and analyzed.

FIG. 5B shows data where Ki-67 and γ-H2AX in tumor tissues were analyzed by IHC staining at the end of experiments and quantified.

FIG. 5C shows data where H1299 lung cancer xenografts were treated with MI-223 (40 mg/kg), Hu (500 mg/kg), or the combination for 25 days.

FIG. 5D shows data where Ki-67 and γ-H2AX in tumor tissues were analyzed by IHC staining at the end of experiments and quantified.

FIG. 6 shows data indication MI-223 potently represses lung cancer in vivo. Nu/Nu nude mice with H1299 lung cancer xenografts were treated with increasing doses of MI-223 (0, 20, 40, 80 and 120 mg/kg/day) for 30 days (n=8 mice per group). Tumor volume was measured once every 2 days. After 30 days, the mice were sacrificed, and the tumors were removed and analyzed.

Figure 7A:
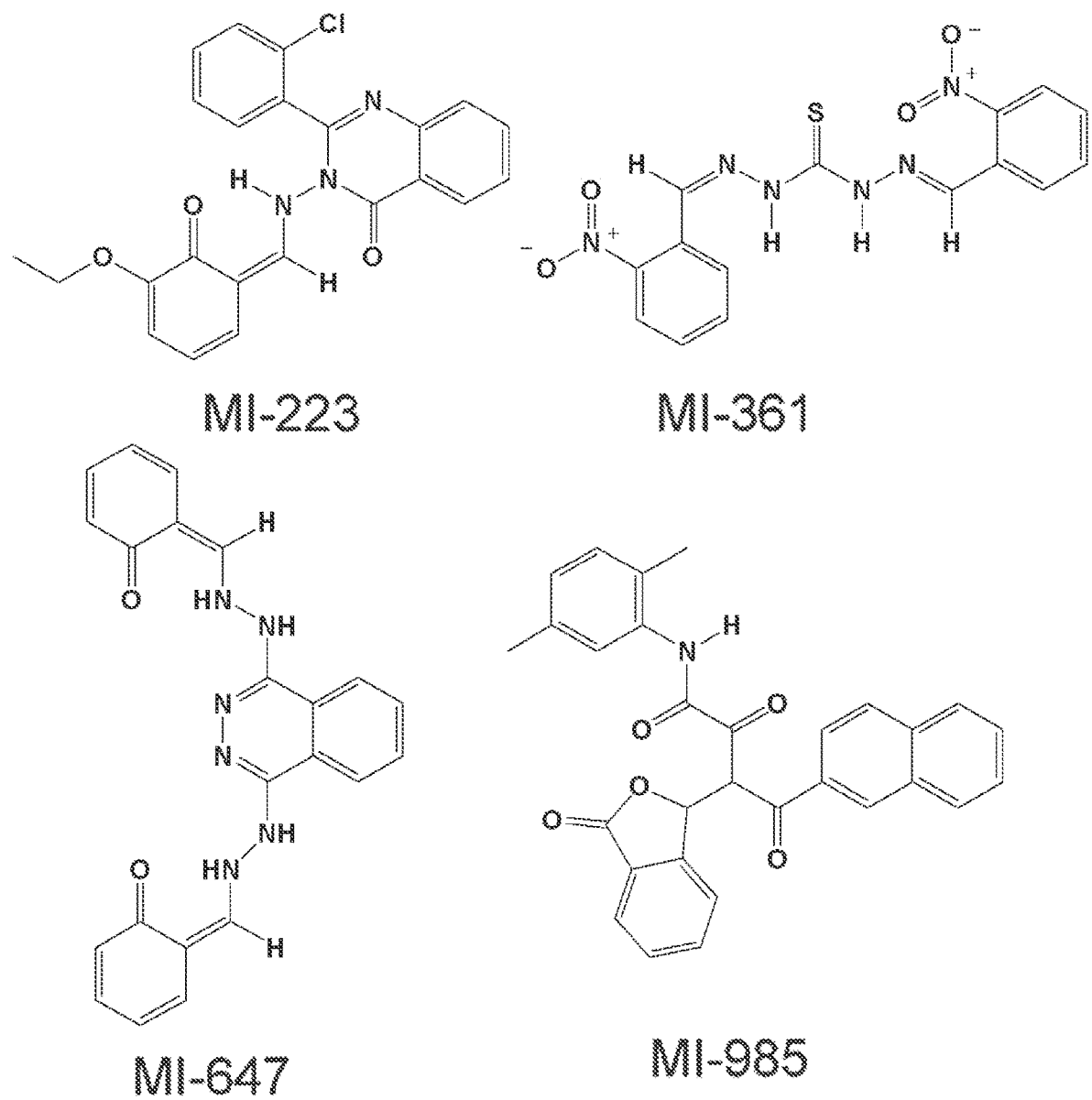

FIG. 7A shows the chemical structures of embodiments of this disclosure.

Figure 7B:
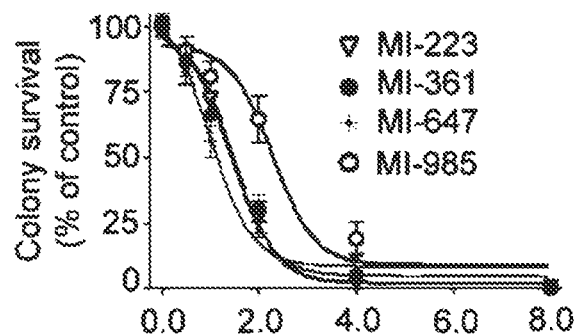

FIG. 7B shows data where H1299 cells were treated with increasing concentrations of the compounds in FIG. 6A followed by colony formation analysis.

Figure 8:
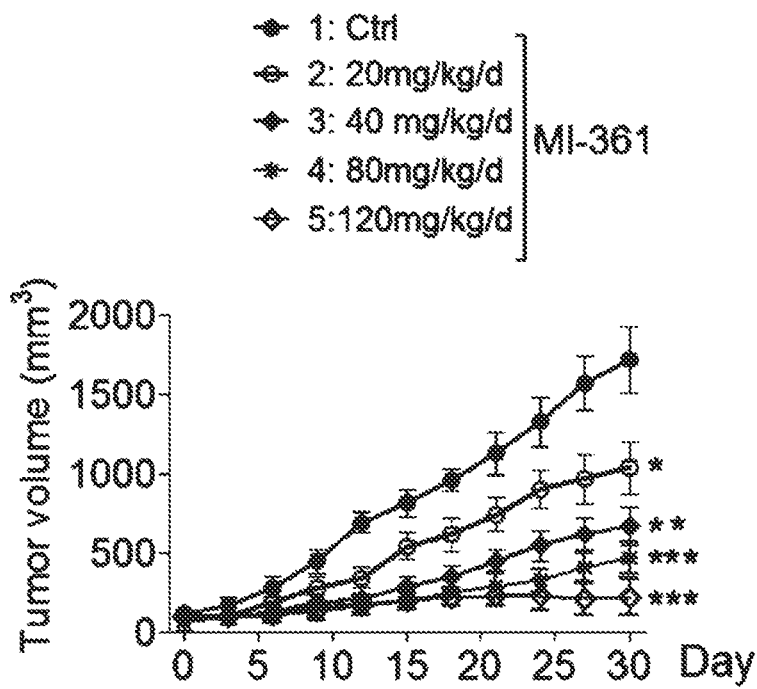

FIG. 8 shows data indicating MI-361 potently represses lung cancer in vivo. Nu/Nu nude mice with H1299 lung cancer xenografts were treated with increasing doses of MI-361 (0, 20, 40, 80 and 120 mg/kg/day) for 30 days. Tumor volume was measured once every 2 days. After 30 days, the mice were sacrificed, and the tumors were removed and analyzed.

Figure 9:
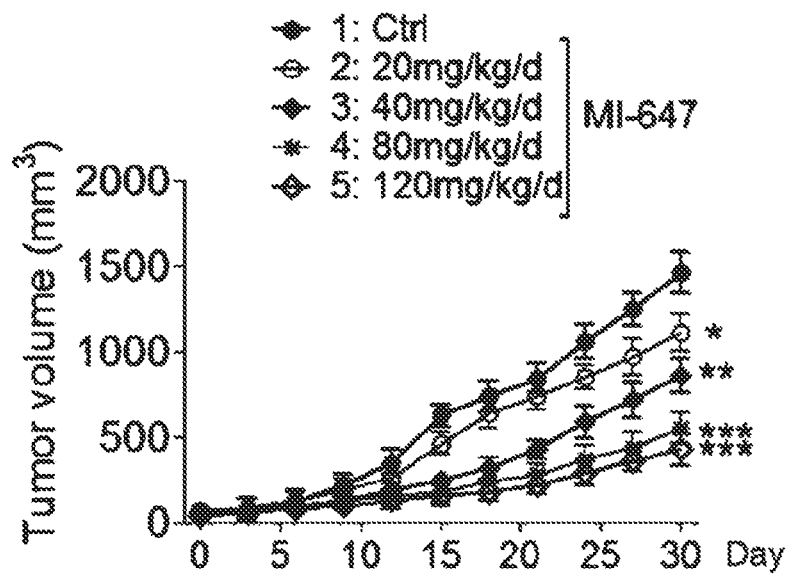

FIG. 9 shows data indicating MI-647 potently represses lung cancer in vivo. Nu/Nu nude mice with H1299 lung cancer xenografts were treated with increasing doses of MI-647 (0, 20, 40, 80 and 120 mg/kg/day) for 30 days. Tumor volume was measured once every 2 days. After 30 days, the mice were sacrificed, and the tumors were removed and analyzed.

Figure 10:
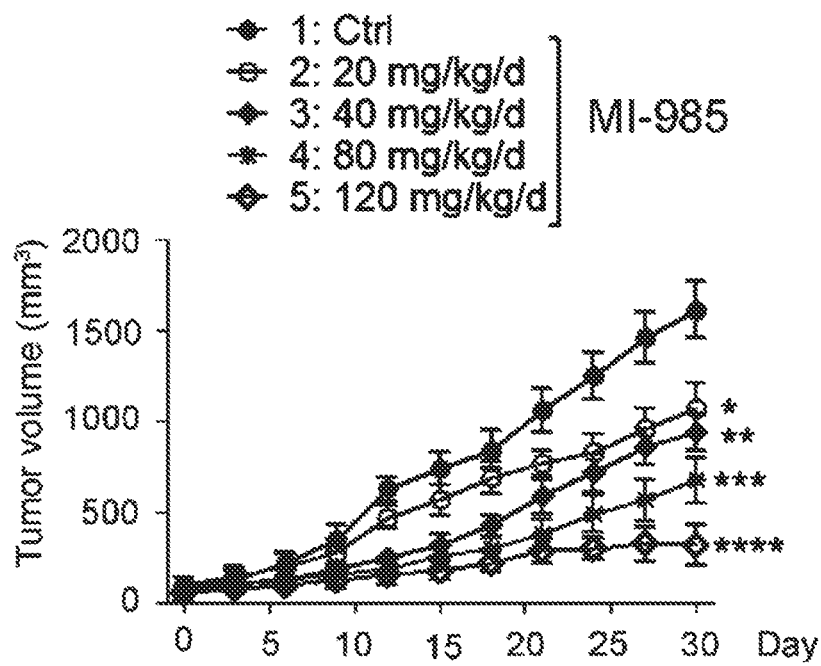

FIG. 10 shows data indicating MI-985 potently represses lung cancer in vivo. (A) Nu/Nu nude mice with H1299 lung cancer xenografts were treated with increasing doses of MI-985 (0, 20, 40, 80 and 120 mg/kg/day) for 30 days (n=8 mice per group). Tumor volume was measured once every 2 days. After 30 days, the mice were sacrificed, and the tumors were removed and analyzed.

DETAILED DISCUSSION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of immunology, medicine, organic chemistry, biochemistry, molecular biology, pharmacology, physiology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

As used herein, the term "derivative" refers to a structurally similar peptide that retains sufficient functional attributes of the identified analogue. The derivative may be structurally similar because it is lacking one or more atoms, e.g., replacing an amino group, hydroxyl, or thiol group with a hydrogen, substituted, a salt, in different hydration/oxidation states, or because one or more atoms within the molecule are switched, such as, but not limited to, replacing a oxygen atom with a sulfur atom or replacing an amino group with a hydroxyl group. The derivative may be a prodrug, comprise a lipid, polyethylene glycol, saccharide, polysaccharide. A derivative may be two or more compounds linked together by a linking group. It is contemplated that the linking group may be biodegradable. Derivatives may be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, —NRaSO$_2$Rb, —C(=O)Ra, —C(=O)ORa, —C(=O)NRaRb, —OC(=O)NRaRb, —ORa, —SRa, —SORa, —S(=O)$_2$Ra, —OS(=O)$_2$Ra and —S(=O)$_2$ORa. Ra and Rb in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, and heteroarylalkyl. The substituents may further optionally be substituted.

The term "optionally substituted," as used herein, means that substitution is optional and therefore it is possible for the designated atom to be unsubstituted.

As used herein, "alkyl" means a noncyclic straight chain or branched, unsaturated or saturated hydrocarbon such as those containing from 1 to 10 carbon atoms, while the term "lower alkyl" or "$C_{1-4}$alkyl" has the same meaning as alkyl but contains from 1 to 4 carbon atoms. The term "higher alkyl" has the same meaning as alkyl but contains from 7 to 20 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Aryl" means an aromatic carbocyclic monocyclic or polycyclic ring such as phenyl or naphthyl. Polycyclic ring systems may, but are not required to, contain one or more non-aromatic rings, as long as one of the rings is aromatic.

As used herein, "heteroaryl" refers to an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above with the indicated number of carbon atoms attached through a sulfur bridge. An example of an alkylthio is methylthio, (i.e., —S—CH3).

"Alkoxy" refers to an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

"Alkylamino" refers to an alkyl group as defined above with the indicated number of carbon atoms attached through an amino bridge. An example of an alkylamino is methylamino, (i.e., —NH—CH3).

"Alkanoyl" refers to an alkyl as defined above with the indicated number of carbon atoms attached through a carbonyl bride (i.e., —(C=O)alkyl).

As used herein, a "lipid" group refers to a hydrophobic group that is naturally or non-naturally occurring that is highly insoluble in water. As used herein a lipid group is considered highly insoluble in water when the point of connection on the lipid is replaced with a hydrogen and the resulting compound has a solubility of less than $0.63 \times 10^{-4}$% w/w (at 25° C.) in water, which is the percent solubility of octane in water by weight. See Solvent Recovery Handbook, $2^{nd}$ Ed, Smallwood, 2002 by Blackwell Science, page 195. Examples of naturally occurring lipids include saturated or unsaturated hydrocarbon chains found in certain fatty acids, glycerolipids, cholesterol, steroids, polyketides, and derivatives. Non-naturally occurring lipids include derivatives of naturally occurring lipids, acrylic polymers, aromatic, and alkylated compounds and derivatives thereof.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In preferred embodiment, the salts are conventional nontoxic pharmaceutically acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The term "prodrug" refers to an agent that is converted into a biologically active form in vivo. Prodrugs are often useful because, in some situations, they may be easier to administer than the parent compound. The prodrug may also have improved solubility in pharmaceutical compositions over the parent drug. A prodrug may be converted into the parent drug by various mechanisms, including enzymatic processes and metabolic hydrolysis. Typical prodrugs are pharmaceutically acceptable esters. Prodrugs include compounds wherein a hydroxy, amino or mercapto (thiol) group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like.

A "linking group" refers to any variety of molecular arrangements that can be used to bridge to molecular moieties together. An example formula may be —$R_m$— wherein R is selected individually and independently at each occurrence as: —$CR_mR_m$—, —$CHR_m$—, —CH—, —C—, —$CH_2$—, —$C(OH)R_m$, —C(OH)(OH)—, —C(OH)H, —$C(Hal)R_m$—, —C(Hal)(Hal)-, —C(Hal)H—, —$C(N_3)R_m$—, —$C(CN)R_m$—, —C(CN)(CN)—, —C(CN)H—, —$C(N_3)(N_3)$—, —$C(N_3)H$—, —O—, —S—, —N—, —NH—, —$NR_m$—, —(C=O)—, —(C=NH)—, —(C=S)—, —(C=$CH_2$)—, which may contain single, double, or triple bonds individually and independently between the R groups. If an R is branched with an $R_m$ it may be terminated with a group such as —$CH_3$, —H, —CH=$CH_2$, —CCH, —OH, —SH, —$NH_2$, —$N_3$, —CN, or -Hal, or two branched Rs may form a cyclic structure. It is contemplated that in certain instances, the total Rs or "m" may be less than 100, or 50, or 25, or 10. Examples of linking groups include bridging alkyl groups and alkoxyalkyl groups. Linking groups may be substituted with one or more substituents.

"Cancer" refers any of various cellular diseases with malignant neoplasms characterized by the proliferation of cells. It is not intended that the diseased cells must actually invade surrounding tissue and metastasize to new body sites. Cancer can involve any tissue of the body and have many different forms in each body area. Within the context of certain embodiments, whether "cancer is reduced" may be identified by a variety of diagnostic manners known to one skill in the art including, but not limited to, observation the reduction in size or number of tumor masses or if an increase of apoptosis of cancer cells observed, e.g., if more than a 5% increase in apoptosis of cancer cells is observed for a sample compound compared to a control without the compound. It may also be identified by a change in relevant biomarker or gene expression profile, such as PSA for prostate cancer, HER2 for breast cancer, or others.

As used herein, "subject" refers to any animal, preferably a human patient, livestock, or domestic pet.

As used herein, the terms "prevent" and "preventing" include the prevention of the recurrence, spread or onset. It is not intended that the present disclosure be limited to complete prevention. In some embodiments, the onset is delayed, or the severity is reduced.

As used herein, the terms "treat" and "treating" are not limited to the case where the subject (e.g. patient) is cured and the disease is eradicated. Rather, embodiments of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

A "chemotherapy agent," "chemotherapeutic," "anti-cancer agent" or the like, refer to molecules that are recognized to aid in the treatment of a cancer. Contemplated examples include the following molecules or derivatives such as alemtuzumab, trastuzumab, ibritumomab tiuxetan, brentuximab vedotin, temozolomide, ado-trastuzumab emtansine, denileukin diftitox, blinatumomab, interferon alpha, aldesleukin, carmustine, bevacizumab, procarbazine, lomustine, vincristine, gefitinib, erlotinib, cisplatin, carboplatin, oxaliplatin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin, mithramycin, vinblastine, vindesine, vinorelbine, paclitaxel, taxol, docetaxel, etoposide, teniposide, amsacrine, topotecan, camptothecin, bortezomib, anagrelide, tamoxifen, toremifene, raloxifene, droloxifene, fulvestrant, bicalutamide, flutamide, nilutamide, cyproterone, goserelin, leuprorelin, buserelin, megestrol, anastrozole, letrozole, vorozole, exemestane, finasteride, marimastat, trastuzumab, cetuximab, dasatinib, imatinib, combretastatin, thalidomide, azacitidine, azathioprine, capecitabine, chlorambucil, cyclophosphamide, cytarabine, daunorubicin, doxifluridine, epothilone, irinotecan, mechlorethamine, mercaptopurine, mitoxantrone, pemetrexed, tioguanine, valrubicin, rituximab, and/or lenalidomide or combinations thereof such as cyclophosphamide, methotrexate, 5-fluorouracil (CMF); doxorubicin, cyclophosphamide (AC); mustine, vincristine, procarbazine, prednisolone (MOPP); adriamycin, bleomycin, vinblastine, dacarbazine (ABVD); cyclophosphamide, doxorubicin, vincristine, prednisolone (CHOP); rituximab, cyclophosphamide, doxorubicin, vincristine, prednisolone (RCHOP); bleomycin, etoposide, cisplatin (BEP); epirubicin, cisplatin, 5-fluorouracil (ECF); epirubicin, cisplatin, capecitabine (ECX); methotrexate, vincristine, doxorubicin, cisplatin (MVAC).

In certain embodiments, treatment of cancer may be combined with another anticancer agent. In certain embodiments, the anti-cancer agent is selected from abemaciclib, abiraterone acetate, methotrexate, paclitaxel, adriamycin, acalabrutinib, brentuximab vedotin, ado-trastuzumab emtansine, aflibercept, afatinib, netupitant, palonosetron, imiquimod, aldesleukin, alectinib, alemtuzumab, pemetrexed disodium, copanlisib, melphalan, brigatinib, chlorambucil, amifostine, aminolevulinic acid, anastrozole, apalutamide, aprepitant, pamidronate disodium, exemestane, nelarabine, arsenic trioxide, ofatumumab, atezolizumab, bevacizumab, avelumab, axicabtagene ciloleucel, axitinib, azacitidine, carmustine, belinostat, bendamustine, inotuzumab ozogamicin, bevacizumab, bexarotene, bicalutamide, bleomycin, blinatumomab, bortezomib, bosutinib, brentuximab vedotin, brigatinib, busulfan, irinotecan, capecitabine, fluorouracil, carboplatin, carfilzomib, ceritinib, daunorubicin, cetuximab, cisplatin, cladribine, cyclophosphamide, clofarabine, cobimetinib, cabozantinib-S-malate, dactinomycin, crizotinib, ifosfamide, ramucirumab, cytarabine, dabrafenib, dacarbazine, decitabine, daratumumab, dasatinib, defibrotide, degarelix, denileukin diftitox, denosumab, dexamethasone, dexrazoxane, dinutuximab, docetaxel, doxorubicin, durvalumab, rasburicase, epirubicin, elotuzumab, oxaliplatin, eltrombopag olamine, enasidenib, enzalutamide, eribulin, vismodegib, erlotinib, etoposide, everolimus, raloxifene, toremifene, panobinostat, fulvestrant, letrozole, filgrastim, fludarabine, flutamide, pralatrexate, obinutuzumab, gefitinib, gemcitabine, gemtuzumab ozogamicin, glucarpidase, goserelin, propranolol, trastuzumab, topotecan, palbociclib, ibritumomab tiuxetan, ibrutinib, ponatinib, idarubicin, idelalisib, imatinib, talimogene laherparepvec, ipilimumab, romidepsin, ixabepilone, ixazomib, ruxolitinib, cabazitaxel, palifermin, pembrolizumab, ribociclib, tisagenlecleucel, lanreotide, lapatinib, olaratumab, lenalidomide, lenvatinib, leucovorin, leuprolide, lomustine, trifluridine, olaparib, vincristine, procarbazine, mechlorethamine, megestrol, trametinib, temozolomide, methylnaltrexone bromide, midostaurin, mitomycin C, mitoxantrone, plerixafor, vinorelbine, necitumumab, neratinib, sorafenib, nilutamide, nilotinib, niraparib, nivolumab, tamoxifen, romiplostim, sonidegib, omacetaxine, pegaspargase, ondansetron, osimertinib, panitumumab, pazopanib, interferon alfa-2b, pertuzumab, pomalidomide, mercaptopurine, regorafenib, rituximab, rolapitant, rucaparib, siltuximab, sunitinib, thioguanine, temsirolimus, thalidomide, thiotepa, trabectedin, valrubicin, vandetanib, vinblastine, vemurafenib, vorinostat, zoledronic acid, or combinations thereof.

Targeting Mcl-1 Enhances DNA Replication Stress Sensitivity to Cancer Therapy

Cells utilize two major pathways for DSB repair: non-homologous end joining (NHEJ) and homologous recombination (HR). NHEJ facilitates DSB repair by direct ligation of broken DNA ends. To initiate NHEJ, the Ku70/Ku80 heterodimer binds to blunt or near-blunt DNA ends. DSB-bound Ku then recruits and activates the DNA-dependent protein kinase catalytic subunit (DNA-PKcs), which triggers a signaling cascade that orchestrates downstream repair processes that eventually seal the breaks. In the HR repair pathway, DSBs are recognized by the MRN (Mre11-Rad50-NBS1) complex and CtIP to initiate DSB end resection leading to generation of 3' single-stranded DNA (ssDNA) overhangs through endonucleolytic cleavage followed by 3'-5' exonucleolytic processing. The 3' ssDNA overhangs are initially coated by the RPA complex to form an RPA-ssDNA nucleoprotein filament to allow extensive resection by the EXO and DNA2 nucleases, followed by displacement of RPA to allow assembly of the Rad51-ssDNA nucleoprotein filament. Rad51 loading promotes invasion onto the undamaged template and strand displacement, generating D-loop formation, which generates a Holliday junction and a heteroduplex molecule. Repair ensues using the undamaged strand as a template, followed by ligation of the DNA ends.

The route of DSB repair pathway has an impact on genomic integrity and the prevention of cancer. DSB repair via HR typically ensures fidelity and reduces the probability of mutation or genomic instability compared with NHEJ, because HR uses an undamaged template with homologous sequences to restore sequence information lost at the DSB site, whereas NHEJ does not require sequence homology for repair. The occurrence of these pathways depends on the phase of the cell cycle and the nature of the DSB ends. NHEJ is believed to be active throughout all phases of the cell cycle but predominates in G1. HR is believed to be more active in S and G2 phases during DNA replication, since an identical sister chromatid is available as a template for repair. A biochemical event influencing DSB repair pathways is competition between Ku-mediated DNA end protection and MRN complex-initiated DNA end resection. For example, initiation of 5'-3' resection of DNA ends by the MRN complex commits cells to HR-dependent repair, and prevents repair by classical NHEJ. Once HR is initiated, it is believed that NHEJ cannot be utilized in most instances. Conversely, once Ku binds dsDNA ends with high affinity, the DSB-bound Ku complex restricts the ability of the MRN complex to initiate DNA resection, which suppresses HR, while, at the same time, promoting NHEJ. A major, unanswered question is how MRN directly or indirectly counteracts NHEJ to promote HR. Experiments were performed to determine whether there is a pathway choice controller that allows NHEJ to predominate in G0/G1 and subsequently switch to the HR pathway in S/G2 during cell cycle progression through regulation of the core DSB repair machinery.

Myeloid cell leukemia sequence 1 (Mcl-1) expression is tightly regulated at multiple levels, including transcriptional, posttranscriptional, and posttranslational processes. In contrast to other anti-apoptotic Bcl-2 family members (i.e., Bcl-2, Bcl-xL, Bcl-w, and Bfl-1A1), Mcl-1 has a considerably longer N-terminus that is intrinsically unstructured and therefore resistant to structural analyses. Mcl-1 is unique with respect to its short half-life (30 minutes to 3 hours) and short-term pro-survival function, which probably relates to the presence of a long proline-, glutamic acid-, serine-, and threonine-rich (PEST) region upstream of the Bcl-2 homology (BH) domain. Mcl-1 expression changes rapidly in response to cellular stresses or cell cycle progression, because its degradation is tightly regulated by three E3 ligases (Mule, FBW7, and (3-TrCP) and two deubiquitinases (USP9X and Ku70). In addition to its cell survival function, Mcl-1 has been demonstrated to regulate ATR-mediated CHK1 phosphorylation and localize to sites of DNA damage in response to DNA damage. Mattoo et al. report that MCL-1 depletion impairs DNA double-strand break repair and re-initiation of stalled DNA replication forks. Mol Cell Biol. 2017; 37(3):e00535-16.

Experiments reported herein indicate that during cell cycle progression, Mcl-1 peaks and selectively interacts with Ku in S/G2 phase, resulting in the suppression of NHEJ while simultaneously promoting DNA resection and activation of the HR pathway. This indicates that Mcl-1, in addition to its anti-apoptotic function, also functions in mediating DSB repair pathway choice. Small molecule that disrupts the Mcl-1/Ku interaction have been discovered to inhibit HR activity and strongly synergizes with DNA replication stress agents (hydroxyurea or olaparib) against lung cancer in vitro and in vivo.

Because DNA end resection is considered a major control point between NHEJ and HR choice, DSB end resection is appropriately restricted to S/G2, as HR requires the presence of an intact sister chromatid to promote repair. Cells favor DSB repair by NHEJ if the DNA ends are suitable for joining, while DNA resection is activated if joining fails, particularly when DNA ends are not suitable for NHEJ. Since Mcl-1 molecules were recruited to DSB sites following the induction of DSBs by IR or I-SceI, this could provide potential for Mcl-1 to be involved in the process of DNA resection. Intriguingly, Mcl-1 facilitates Mre11 complex-mediated DNA resection in a mechanism involving inhibition of Ku/DSB binding via direct interaction with Ku proteins, suggesting that Mcl-1 binding to Ku may release Ku from DSBs to initiate Mre11 complex-mediated DNA resection leading to promotion of HR. The positive effect of Mcl-1 on DNA resection and HR accelerates the repair of DNA replication stress-induced DSBs. Selective promotion of HR-dependent DSB repair by Mcl-1 might play an important role in prolonging cell survival following DNA replication stress.

Domain-mapping studies reveal that Mcl-1 directly interacts with the Ku70/Ku80 dimer via its BH1 and BH3 domains. Importantly, these 2 Ku binding sites on Mcl-1 are important not only for its inhibitory effect on NHEJ but also for its positive effects on DNA end resection and HR-mediated DSB repair, which indicates that the mechanism of action of Mcl-1 in directing DSB repair pathway choice and increasing clonogenic survival following treatment with DNA replication stress agents.

Inhibition of apoptosis by Mcl-1 occurs through its heterodimerization with multiple pro-apoptotic Bcl-2 family proteins (i.e., Bim, Bak, or Bax) within the mitochondrial membranes. In addition to this anti-apoptotic mechanism, experiments described herein indicate that Mcl-1 not only regulates the choice between HR and NHEJ, but also supports clonogenic cell survival through promotion of HR-dependent DSB repair following Hu- or olaparib-induced DNA replication stress. This activity is believed to contribute to therapeutic resistance in human cancers.

In addition to its mitochondrial localization, Mcl-1 has also been shown to be localized in the nucleus with levels peaking in S/G2. Selective expression of Mcl-1 in the nucleus facilitates HR-dependent DSB repair leading to increased clonogenic survival following DNA replication stress-induced DSBs. However, nuclear Mcl-1 does not have an anti-apoptotic function, as evidenced by the inability of the nuclear-targeted Mcl-1 to support survival following treatment with the apoptotic agent staurosporine. It may be that nuclear Mcl-1 promotes HR-dependent DSB repair while mitochondrial Mcl-1 may inhibit apoptosis.

Using a NCI small-molecule library and the UCSF DOCK 6.1 screen program, MI-223 was identified as a lead compound that directly binds to Mcl-1 protein via its BH1 domain and disrupts the interaction between Mcl-1 and Ku. MI-223 induces robust cancer cell killing via inhibition of HR-mediated DNA repair. Importantly, MI-223-mediated reduction of HR activity renders cancer cells highly sensitive to DNA replication stress agents (Hu or olaparib). This observation helps to explain why the combination of MI-223 with Hu or olaparib displayed strong synergism against lung cancer in mouse xenografts.

Experiment reported herein indicate that Mcl-1 is involved in the regulation of NHEJ- and HR-mediated DNA repair pathway choice. Physiologic accumulation of Mcl-1 in S/G2 phase renders a net increase of HR over NHEJ. Direct interaction of Mcl-1 with Ku via its BH1 and BH3 domains is required for Mcl-1 inhibition of Ku-DNA binding, promotion of Mre11 complex-mediated DNA resection, and enhancement of HR activity, resulting in HR-dependent DSB repair and increased cell survival. Therefore, Mcl-1, in addition to its anti-apoptotic function, appears to be a driver of the mechanism utilized for choice of DSB repair pathway. Specifically targeting Mcl-1 represents an effective strategy for cancer therapy.

Compounds that Inhibits Mcl-1-Stimulated Homologous Recombination DNA Repair

Although it is not intended that certain embodiments of this disclosure be limited by any particular mechanism, it is believed that certain compounds inhibit Mcl-1-stimulated homologous recombination DNA repair, such as, 2-(2-chlorophenyl)-3-(((5-ethoxy-6-oxocyclohexa-2,4-dien-1-ylidene)methyl)amino)quinazolin-4(3H)-one, salts, or derivatives thereof. In certain embodiments, a compound useful in compositions disclosed herein and for methods, described herein, has the following formula I:

Formula I

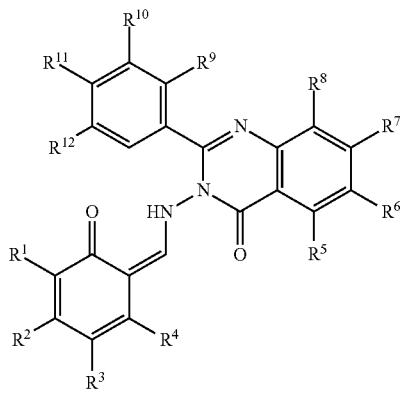

or salts or derivatives thereof wherein, $R^1$, $R^2$, $R^3$, $R^4$, $R^5$, $R^6$, $R^7$, $R^8$, $R^9$, $R^{10}$, $R^{11}$, and $R^{12}$, are individually and independently selected from hydrogen, halogen, alkyl, hydroxy, alkoxy, mercapto, alkylthiol, amino, alkylamino, dialkylamino, nitro, and nitrile.

In certain embodiments, $R^1$ is alkoxy.

In certain embodiments, $R^9$ is halogen.

In certain embodiments, a compound that is believed to inhibit Mcl-1-stimulated homologous recombination DNA repair is N'-(2-nitrobenzylidene)-2-(2-nitrobenzylidene)hydrazine-1-carbothiohydrazide, salts, or derivatives thereof. In certain embodiments, a compound useful in compositions disclosed herein and for methods, described herein, has the following formula II:

Formula II

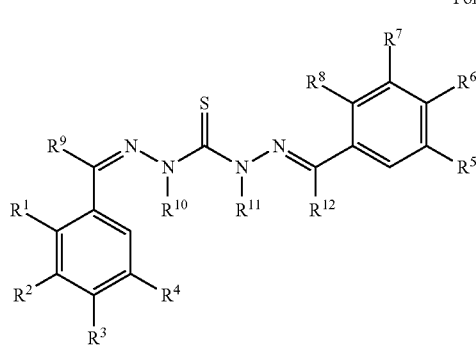

or salts or derivatives thereof wherein, $R^1$, $R^2$, $R^3$, $R^4$, $R^5$, $R^6$, $R^7$, $R^8$, $R^9$, $R^{10}$, $R^{11}$, and $R^{12}$, are individually and independently selected from hydrogen, halogen, alkyl, hydroxy, alkoxy, mercapto, alkylthiol, amino, alkylamino, dialkylamino, nitro, and nitrile.

In certain embodiments, $R^1$ is nitro.

In certain embodiments, $R^8$ is nitro.

In certain embodiments, $R^9$, $R^{10}$, $R^{11}$, and $R^{12}$, are hydrogen.

In certain embodiments, a compound that is believed to inhibit Mcl-1-stimulated homologous recombination DNA repair is 6,6'-((phthalazine-1,4-diylbis(hydrazine-2,1-diyl))bis(methanylylidene))bis(cyclohexa-2,4-dien-1-one), salts, or derivatives thereof. In certain embodiments, a compound useful in compositions disclosed herein and for methods, described herein, has the following formula III:

Formula III

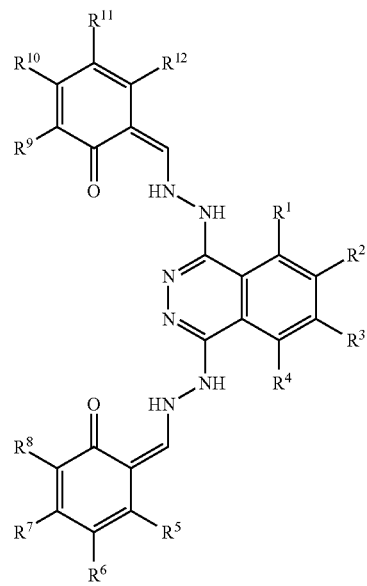

or salts or derivatives thereof wherein, $R^1$, $R^2$, $R^3$, $R^4$, $R^5$, $R^6$, $R^7$, $R^8$, $R^9$, $R^{10}$, $R^{11}$, and $R^{12}$, are individually and independently selected from hydrogen, halogen, alkyl, hydroxy, alkoxy, mercapto, alkylthiol, amino, alkylamino, dialkylamino, nitro, and nitrile.

In certain embodiments, a compound that is believed to inhibit Mcl-1-stimulated homologous recombination DNA repair is N-(2,5-dimethylphenyl)-4-(naphthalen-2-yl)-2,4-dioxo-3-(3-oxo-1,3-dihydroisobenzofuran-1-yl)butanamide, salts, or derivatives thereof. In certain embodiments, a compound useful in compositions disclosed herein and for methods, described herein, has the following formula IV:

Formula IV

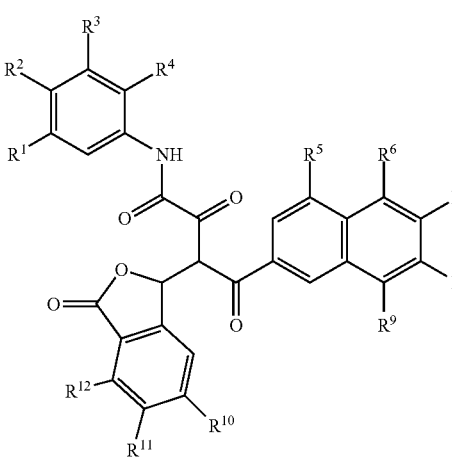

or salts or derivatives thereof wherein, $R^1$, $R^2$, $R^3$, $R^4$, $R^5$, $R^6$, $R^7$, $R^8$, $R^9$, $R^{10}$, $R^{11}$, and $R^{12}$, are individually and independently selected from hydrogen, halogen, alkyl, hydroxy, alkoxy, mercapto, alkylthiol, amino, alkylamino, dialkylamino, nitro, and nitrile.

Formulations

Pharmaceutical compositions disclosed herein can be in the form of pharmaceutically acceptable salts, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below).

When the compounds of the disclosure contain an acidic group as well as a basic group, the compounds of the disclosure can also form internal salts, and such compounds are within the scope of the disclosure. When a compound contains a hydrogen-donating heteroatom (e.g. NH), salts are contemplated to cover isomers formed by transfer of the hydrogen atom to a basic group or atom within the molecule.

Pharmaceutically acceptable salts of the compounds include the acid addition and base salts thereof. Suitable acid addition salts are formed from acids that form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases that form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases can also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein can be administered in the form of prodrugs. A prodrug can include a covalently bonded carrier that releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a mammalian subject, cleaves to form a free hydroxyl group. Examples of prodrugs include, but are not limited to, acetate, formate and benzoate derivatives of alcohol functional groups in the compounds. Examples of structuring a compound as prodrugs can be found in the book of Testa and Caner, Hydrolysis in Drug and Prodrug Metabolism, Wiley (2006) hereby incorporated by reference. Typical prodrugs form the active metabolite by transformation of the prodrug by hydrolytic enzymes, the hydrolysis of amides, lactams, peptides, carboxylic acid esters, epoxides or the cleavage of esters of inorganic acids.

Pharmaceutical compositions typically comprise an effective amount of a compound and a suitable pharmaceutical acceptable carrier. The preparations can be prepared in a manner known per se, which usually involves mixing the at least one compound according to the disclosure with the one or more pharmaceutically acceptable carriers, and, if desired, in combination with other pharmaceutical active compounds, when necessary under aseptic conditions. Reference is made to U.S. Pat. Nos. 6,372,778, 6,369,086, 6,369,087 and 6,372,733 and the further references mentioned above, as well as to the standard handbooks, such as the latest edition of Remington's Pharmaceutical Sciences. It is well known that ester prodrugs are readily degraded in the body to release the corresponding alcohol. See e.g., Imai, Drug Metab Pharmacokinet. (2006) 21(3):173-85, entitled "Human carboxylesterase isozymes: catalytic properties and rational drug design."

Generally, for pharmaceutical use, the compounds can be formulated as a pharmaceutical preparation comprising at least one compound and at least one pharmaceutically acceptable carrier, diluent or excipient and/or adjuvant, and optionally one or more further pharmaceutically active compounds.

The pharmaceutical preparations of the disclosure are preferably in a unit dosage form, and can be suitably packaged, for example in a box, blister, vial, bottle, sachet, ampoule or in any other suitable single-dose or multi-dose holder or container (which can be properly labeled); optionally with one or more leaflets containing product information and/or instructions for use. Generally, such unit dosages will contain between 1 and 1000 mg, and usually between 5 and 500 mg, of the at least one compound of the disclosure e.g., about 10, 25, 50, 100, 200, 300 or 400 mg per unit dosage.

The compounds can be administered by a variety of routes including the oral, ocular, rectal, transdermal, subcutaneous, intravenous, intramuscular or intranasal routes, depending mainly on the specific preparation used. The compound will generally be administered in an "effective amount," by which it is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which can be administered as a single daily dose, divided over one or more daily doses. The amount(s) to be administered, the route of administration and the further treatment regimen can be determined by the treating clinician, depending on factors such as the age, gender and general condition of the patient and the nature and severity of the disease/symptoms to be treated. Reference is made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

Formulations containing one or more of the compounds described herein can be prepared using a pharmaceutically acceptable carrier composed of materials that are considered safe and effective and can be administered to an individual without causing undesirable biological side effects or unwanted interactions. The carrier is all components present in the pharmaceutical formulation other than the active ingredient or ingredients. As generally used herein "carrier" includes, but is not limited to, diluents, binders, lubricants, disintegrators, fillers, pH modifying agents, preservatives, antioxidants, solubility enhancers, and coating compositions.

Carrier also includes all components of the coating composition that can include plasticizers, pigments, colorants, stabilizing agents, and glidants. Delayed release, extended release, and/or pulsatile release dosage formulations can be prepared as described in standard references such as "Pharmaceutical dosage form tablets," Edition, Liberman et al. (New York, Marcel Dekker, Inc., 1989), "Remington—The science and practice of pharmacy," 20th ed., Lippincott Williams & Wilkins, Baltimore, Md., 2000, and "Pharmaceutical dosage forms and drug delivery systems," 6th Edition, Ansel et al., (Media, Penn.: Williams and Wilkins, 1995). These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins, zein, shellac, and polysaccharides.

Additionally, the coating material can contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants.

Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet, bead, or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, arginine, gums or cross linked polymers, such as cross-linked PVP.

Stabilizers are used to inhibit or retard drug decomposition reactions that include, by way of example, oxidative reactions.

Surfactants can be anionic, cationic, amphoteric or nonionic surface-active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, stearoyl monoisopropanolamide, and polyoxyethylene hydrogenated tallow amide. Examples of amphoteric surfactants include sodium N-dodecyl-.beta.-alanine, sodium N-lauryl-beta-iminodipropionate, myristoamphoacetate, lauryl betaine and lauryl sulfobetaine.

If desired, the tablets, beads, granules, or particles can also contain minor amount of nontoxic auxiliary substances such as wetting or emulsifying agents, dyes, pH buffering agents, or preservatives.

The compositions described herein can be formulation for modified or controlled release. Examples of controlled release dosage forms include extended release dosage forms, delayed release dosage forms, pulsatile release dosage forms, and combinations thereof.

The extended release formulations are generally prepared as diffusion or osmotic systems, for example, as described in "Remington—The science and practice of pharmacy" (20th ed., Lippincott Williams & Wilkins, Baltimore, Md., 2000). A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly (methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules. An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

Delayed release formulations are created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition can be, e.g., a tablet for incorporation into a capsule, a tablet for use as an inner core in a "coated core" dosage form, or a plurality of drug-containing beads, particles or granules, for incorporation into a tablet or capsule. Preferred coating materials include bioerodible, gradually hydrolyzable, gradually water-soluble, and/or enzymatically degradable polymers, and can be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins; vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials can also be used. Multi-layer coatings using different polymers can also be applied.

The preferred coating weights for particular coating materials can be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition can include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates can also be used. Pigments such as titanium dioxide can also be used. Small quantities of an anti-foaming agent, such as a silicone (e.g., simethicone), can also be added to the coating composition.

Alternatively, each dosage unit in the capsule can comprise a plurality of drug-containing beads, granules or particles. As is known in the art, drug-containing "beads" refer to beads made with drug and one or more excipients or polymers. Drug-containing beads can be produced by applying drug to an inert support, e.g., inert sugar beads coated with drug or by creating a "core" comprising both drug and one or more excipients. As is also known, drug-containing "granules" and "particles" comprise drug particles that can or cannot include one or more additional excipients or polymers. In contrast to drug-containing beads, granules and particles do not contain an inert support. Granules generally comprise drug particles and require further processing. Generally, particles are smaller than granules, and are not further processed. Although beads, granules and particles can be formulated to provide immediate release, beads and granules are generally employed to provide delayed release.

EXAMPLES

Mcl-1 Facilitates Recruitment of Mre11 to DSBs Via Direct Interaction with Ku.

To test whether Mcl-1 affects the recruitment of factors regulating HR (i.e., Mre11) or NHEJ (i.e., Ku70/Ku80) to DSB sites, a ChIP assay was performed following induction of DSBs with I-SceI in DR-GFP MEFs or DR-GFP U2OS cells. Two pairs of primers, located 200 bp upstream or downstream of the I-SceI site, were used to determine the relative abundance of Mre11 and Ku70 at the induced break site. Levels of Ku70 at DSBs induced by I-SceI were lower in WT MEFs compared with Mcl1−/− MEFs. Conversely, levels of Mre11 recruited to DSBs were significantly higher in WT MEFs compared with Mcl1−/− MEFs (barely detectable in Mcl1−/− MEFs). Similar results were also observed in U2OS DR-GFP cells when Mcl-1 was knocked down with Mcl-1 siRNA. These results indicate that Mcl-1 is essential for recruitment of Mre11 to the DSB site. Thus, the negative effect of Mcl-1 on Ku70 recruitment, and its positive effect on Mre11 recruitment following DSB induction, may be an important factor for pathway choice in DSB repair.

Mcl-1 was enhanced in S/G2, but total levels of Ku70/Ku80 and Mre11 did not change during cell cycle progression. To test whether Mcl-1 associates with factors regulating NHEJ and HR, co-immunoprecipitation (co-IP) was performed in H1299 cells during cell cycle progression. Mcl-1 selectively interacted with Ku70/Ku80 but not Mre11, peaking at S/G2 phase. To further assess whether cell cycle progression affects subcellular localization of Mcl-1 and Ku, G1- and S/G2-phase H1299 cells were isolated from double-thymidine block synchronization. Subcellular fractionation experiments were then performed to isolate heavy membrane-containing mitochondria, light membrane-containing endoplasmic reticulum, and nuclear (Nuc) fractions from G1- or S/G2-phase H1299 cells. Levels of Ku70 and Mcl-1 in each fraction were quantified from Western blot by ImageJ software (NIH). In G1-phase cells, the majority of Mcl-1 (86%) was localized in mitochondria and only a small portion of Mcl-1 was localized in the endoplasmic reticulum (8%) and nucleus (6%), while Ku70 and Ku80 were localized only in the nucleus. When cells entered S/G2 phase, the distribution of Mcl-1 in the nuclear fraction was significantly enhanced (i.e., from 6% to 40%), thus having great potential to colocalize and/or interact with Ku proteins in the nucleus.

To test whether replication stress affects the Mcl-1/Ku interaction, time course experiments were carried out. H1299 cells were treated with Hu or olaparib for various times (0, 0.5, 1, 2, 8, or 24 hours). The Mcl-1/Ku interaction and cell cycle were analyzed simultaneously at each time point. Mcl-1/Ku interaction was increased at 2, 8, and 24 hours following treatment of cells with Hu or olaparib. However, Hu treatment did not alter the percentage of cells in S phase at short time points (i.e., 2 and 8 hours), and the percentage of cells in S phase was enhanced only at the 24-hour time point, indicating that increased Mcl-1/Ku interaction also occurs before cells enter S phase following Hu treatment. Intriguingly, treatment of H1299 cells with olaparib did not significantly affect the percentage of S phase cells at time points tested, but increased Mcl-1/Ku interactions were observed at 2, 8, and 24 hours. These findings indicate that, in addition to S/G2 cell cycle phase, Hu- or olaparib-induced DNA replication stress can also promote Mcl-1/Ku interaction.

Mcl-1 Directly Interacts with Ku Via BH1 and BH3 Domains, Leading to Suppression of Ku-DNA Binding Activity.

Mcl-1 contains multiple functional domains, including N-terminal, PEST, BH1, BH2, BH3, and transmembrane (TM) domains. To identify the binding region of Mcl-1 to Ku, a panel of Mcl-1 deletion mutants, including ΔN (aa 10-120), ΔPEST (aa 120-200), ΔBH1 (aa 256-265), ΔBH2 (aa 305-315), ΔBH3 (aa 213-221), and ΔTM (aa 329-346), were generated (FIG. 1A). Purified recombinant glutathione S-transferase-fused (GST-fused) Mcl-1 WT or deletion mutants were incubated with purified Ku70/Ku80 complex. GST pull-down experiments revealed that WT, ΔN, ΔPEST, ΔBH2, and ΔTM, but not ΔBH1 or ΔBH3, Mcl-1 mutants directly interact with Ku70/Ku80 heterodimer (FIG. 1B), indicating that the BH1 and BH3 domains comprise the Ku binding sites on Mcl-1 protein. To further test this, FLAG-tagged Mcl-1 WT and deletion mutants were exogenously expressed in Mcl1−/− MEFs, followed by co-IP using a FLAG antibody. Similarly, deletion of the BH1 or BH3 domain resulted in loss of Mcl-1's ability to interact with Ku proteins in cells (FIG. 1C).

Since Mcl-1 selectively binds to Ku but not Mre11, the effect of Mcl-1 on Ku-DNA binding or Mre11-DNA binding was compared by EMSA. Recombinant human Mre11-Rad50 (MR) complex was expressed and purified from baculovirus-infected Sf9 insect cells (FIG. 1D). Ku70/Ku80 heterodimer displayed binding to a 32P-labeled, 3' overhang DNA substrate with high affinity, while the MR complex displayed low binding affinity (FIG. 1E, lane 3 vs. lane 7). Addition of purified Mcl-1 suppressed Ku-DNA binding in a dose-dependent manner (FIG. 1E, lane 3 vs. lanes 4-6) but had no significant effect on MR-DNA binding (FIG. 1E, lane 7 vs. lanes 8-10).

These results indicate that purified Mcl-1 protein can directly disrupt Ku-DNA binding but not MR-DNA binding. To further address whether the Mcl-1/Ku interaction is essential for Mcl-1 disruption of Ku-DNA binding, similar experiments using purified recombinant Mcl-1 WT or deletion mutants were carried out. Notably, WT, ΔN, ΔPEST, ΔBH2, and ΔTM, but not ΔBH1 and ΔBH3, Mcl-1 mutants suppressed Ku-DNA binding (FIG. 1F), suggesting that the Ku binding site(s) on Mcl-1 (i.e., BH1 or BH3) is required for Mcl-1-mediated dissociation of the Ku/DNA complex in a cell-free system. The sequence of addition in the above experiments was DNA→Ku→Mcl-1. To test whether the effect of purified Mcl-1 on Ku binding to DNA depends on the order of addition, experiments were also performed with the following order of addition: DNA→Mcl-1→Ku, or DNA→Ku→Mcl-1. Similar results were observed, indicating that the effect of purified Mcl-1 on Ku-DNA binding is independent of the order of addition. These findings suggest that Mcl-1 protein may not only block the interaction of Ku with DNA but may also have the capacity to dissociate Ku from the Ku/DNA complex.

To further test the effect of ΔBH1 and ΔBH3 Mcl-1 mutants on the recruitment of Ku to DSBs in cells, first, WT, ΔBH1, and ΔBH3 mutant Mcl-1 was transfected into Mcl-1-knockout DR-GFP H1299 (Mcl1−/− H1299 DR-GFP) cells, followed by transfection of I-SceI into cells to produce DSBs. ChIP experiments to measure the level of Ku recruitment to DSBs were performed using anti-Ku70 antibody. Results indicated that knockout of endogenous Mcl-1 resulted in increased Ku70 recruitment to DSBs. Intriguingly, expression of endogenous or exogenous WT Mcl-1 but not the Ku binding-deficient Mcl-1 ΔBH1 and ΔBH3 mutants in Mcl-1-knockout H1299 DR-GFP cells reduced Ku recruitment to DSBs, indicating that the Ku binding-deficient ΔBH1 and ΔBH3 Mcl-1 mutants failed to prevent Ku recruitment to DSBs.

Mcl-1 Molecules can be Recruited to DSB Sites Following DNA DSBs.

To address how Mcl-1 has the capacity to inhibit Ku even when there are relatively low levels of Mcl-1 in the nucleus, whether Mcl-1 can be recruited to DNA DSBs was assessed. I-SceI was transfected into U2OS DR-GFP cells to induce DSBs, followed by ChIP using Mcl-1 antibody and PCR to detect DR-GFP break DNA fragment. Results indicated that Mcl-1 was associated with I-SceI-induced DSBs. To further test whether Mcl-1 could be recruited to DSB sites following radiation, S/G2-phase H1299 cells harvested at 6 hours after double-thymidine block were exposed to IR (5 Gy), followed by co-staining with Mcl-1 and γ-H2AX. Intriguingly, Mcl-1 molecules were mainly enriched on DSB sites to form foci and colocalized with γ-H2AX (i.e., a classic DSB marker). The accumulation of Mcl-1 proteins on DSBs could yield a sufficiently high number of Mcl-1 molecules to inhibit Ku at DNA break sites. BH1 and BH3 domains of Mcl-1 are required for its enhancement of HR and suppression of NHEJ.

To further test whether Mcl-1/Ku binding influences NHEJ and HR activities, WT and the panel of Mcl-1 deletion mutants were stably expressed in Mcl1−/− MEFs. Expression levels of the endogenous Mcl-1 in intact WT MEF cells and exogenously expressed Mcl-1 in Mcl1−/− MEF cells were simultaneously analyzed by Western blot using Mcl-1 antibody. Results revealed that knockout of endogenous Mcl-1 resulted in downregulation of HR activity and upregulation of NHEJ activity. Intriguingly, expression of exogenous WT, ΔN, ΔPEST, ΔBH2, and ΔTM, but not ΔBH1 and ΔBH3, Mcl-1 mutants restored HR and suppressed NHEJ activity, but did not significantly affect the percentage of cells in S and G2 phases of the cell cycle or the proliferation rate. These findings suggest that Mcl-1/Ku binding via the BH1 and BH3 domains is an important component for Mcl-1 enhancement of HR activity via inhibition of NHEJ. This data also provided information on the relative levels of endogenous Mcl-1 in intact WT MEF cells compared with exogenously expressed Mcl-1 in Mcl1−/− MEF cells, which could efficiently regulate HR or NHEJ in cells.

Mcl-1 Reverses the Inhibitory Effect of Ku on Mre11 Complex-Induced DNA End Resection.

HR repair is initiated by DSB end resection that is mediated by the Mre11 complex, whereas Ku tightly bound to DNA ends blocks Mre11 DNA resection. As Mcl-1 negatively regulates Ku function via direct binding, Mcl-1 may reverse the Ku-mediated inhibitory effect on Mre11 complex-mediated DNA end resection. Mre11-Rad50 complex-mediated exonuclease activity was analyzed in the presence of increasing concentrations of Mcl-1 protein using 5'-32P-end-labeled fork DNA as a substrate. The Mre11 complex exhibited potent DNA resection activity (FIG. 2A, lane 2 vs. lane 1). Ku heterodimer inhibited MR-mediated DNA resection (FIG. 2A, lane 3 vs. lane 2), which was gradually reversed by the addition of increasing concentrations of purified Mcl-1 protein in the presence of a constant amount of Ku protein (FIG. 2A, lane 3 vs. lanes 4-7). BSA was used as control and had no effect on DNA resection. However, deletion of BH1 or BH3 resulted in the failure of Mcl-1 to reverse the inhibitory effect of Ku on Mre11 complex-mediated DNA resection (FIG. 2B, lanes 3 and 4 vs. lanes 7 and 9), indicating that Mcl-1/Ku binding is required for Mcl-1 to promote DNA resection. In addition, RPA2 is an established reporter of DNA end resection during HR repair in cells. To further test the effect of Mcl-1 on DNA resection in cells, RPA2 foci formation following treatment with Hu, camptothecin (CPT), or IR was compared in WT and Mcl1−/− MEFs. WT and Mcl1−/− MEF cells were treated with Hu (0.2 mM) for 24 hours or CPT (1 μM) for 1 hour, or exposed to IR (5 Gy), followed by immunostaining with anti-RPA2 antibody. Results indicated that IR and CPT as well as Hu induced RPA2 foci formation in WT MEF cells. Knockout of Mcl-1 significantly decreased IR-, CPT-, or Hu-induced RPA2 foci (FIG. 2C). Furthermore, RPA2 phosphorylation at Ser4 and Ser8 has also been extensively used as a surrogate marker for DNA end resection. RPA2 phosphorylation at Ser4 and Ser8 was analyzed by Western blot using the S4/S8 dual-site phosphospecific RPA2 antibody following exposure of MEF WT or MEF Mcl1−/− cells to IR, CPT, and Hu. Results indicate that IR, CPT, and Hu stimulated RPA2 phosphorylation at S4 and S8, and knockout of Mcl-1 reduced RPA2 phosphorylation (FIG. 2D), indicating that depletion of Mcl-1 suppresses DNA end resection. Thus, Mcl-1 may also promote DNA resection in cells.

Expression of Mcl-1 Accelerates Repair of DNA Replication Stress-Induced DSBs Leading to Prolonged Clonogenic Survival, Requiring BH1 and BH3 Domains.

Knockout of Mcl-1 resulted in impairment of HR-mediated DSB repair. To test whether expression of exogenous Mcl-1 restores HR-mediated DSB repair capacity, FLAG-tagged WT and a panel of Mcl-1 deletion mutants were expressed in Mcl1−/− MEFs (FIG. 3A). Hu-induced DNA replication stress led to formation of γ-H2AX DSB foci in MEFs expressing Mcl-1 WT or various deletion mutants (FIG. 3B). After removal of Hu from the medium for 24 hours, most DSB foci disappeared in MEFs expressing WT, ΔN, ΔPEST, ΔBH2, and ΔTM Mcl-1 deletion mutants (FIG. 3B), indicating that Hu-induced DSBs were repaired within 24 hours. However, a significant number of DSB foci persisted in cells expressing ΔBH1, ΔBH3, or vector-only control (FIG. 3B). Since the repair of DNA replication stress-induced DSBs mainly occurs through the HR pathway, these results indicate that Mcl-1 can restore HR activity to repair Hu-induced DSBs, which requires its BH1 and BH3 domains. Furthermore, expression of exogenous WT, ΔN, ΔPEST, ΔBH2, or ΔTM Mcl-1 deletion mutants restored clonogenic survival to different extents following Hu treatment, whereas deletion of the BH1 or BH3 domain resulted in failure of Mcl-1 to restore clonogenic survival (FIG. 3C).

Nuclear Mcl-1 Promotes DSB Repair and Prolongs Clonogenic Survival Following DNA Replication Stress.

In addition to mitochondria, Mcl-1 levels are also elevated in nuclei of S- and G2-phase cells. However, the exact role of nuclear Mcl-1 remains unknown. A nuclear-targeted Mcl-1 construct (Nuc-Mcl-1) was created and transfected into H1299 Mcl-1-knockout cells. Expression of Nuc-Mcl-1 was analyzed by immunostaining. Nuc-Mcl-1 was exclusively expressed in nuclei. To test the role of Nuc-Mcl-1 in the repair of DNA replication stress-induced DSBs, H1299 Mcl-1-knockout cells expressing exogenous Nuc-WT, Nuc-ΔBH1, or Nuc-ΔBH3 mutant Mcl-1 were treated with Hu (0.2 mM) for 24 hours. Following removal of Hu, cells were released into normal culture medium for an additional 6 hours. DSBs were analyzed by immunostaining with γ-H2AX. Hu induced significant DSBs in H1299 Mcl-1-knockout cells expressing Nuc-WT, Nuc-ΔBH1, or Nuc-ΔBH3 mutant Mcl-1 or empty vector control. Following depletion of Hu, a number of γ-H2AX foci were still observed in H1299 Mcl-1-knockout cells transfected with the empty vector control. Intriguingly, γ-H2AX foci were almost undetectable in cells that expressed Nuc-WT Mcl-1. These results indicate that nuclear WT Mcl-1 significantly promotes the repair of DNA replication stress-induced DSBs. However, a significant number of DSB foci persisted in cells expressing Nuc-ΔBH1 or Nuc-ΔBH3 6 hours after Hu depletion, suggesting that the BH1 and BH3 domains are important for Nuc-Mcl-1 to promote DSB repair. To further test the effect of Nuc-Mcl-1 on cell survival, clonogenic survival experiments were carried out following treatment of cells with Hu or staurosporine. Expression of Nuc-WT but not Nuc-ΔBH1 or Nuc-ΔBH3 mutant Mcl-1 prolonged clonogenic cell survival after Hu treatment but had no effect following staurosporine exposure, indicating that Nuc-Mcl-1 enhances clonogenic survival through promoting repair of Hu-induced DSBs but has no anti-apoptotic function in staurosporine-induced mitochondria-dependent apoptosis.

Small Molecule MI-223 Targets the BH1 Binding Pocket of Mcl-1, Reduces HR Efficiency, and Inhibits HR-Mediated DNA Repair, Leading to Synergism with DNA Replication Stress Agents Against Lung Cancer In Vitro and In Vivo.

The BH1 and BH3 domains of Mcl-1 are important to enhance HR and prolong clonogenic survival following DNA replication stress, indicating that BH1 or BH3 is an attractive target for screening small molecules to interfere with HR DNA repair and potentially sensitize cancer cells to DNA replication stress. A National Cancer Institute (NCI) database library of 300,000 small molecules was docked into the Mcl-1 BH1 structure pocket (aa 256-265) identified by the UCSF DOCK 6.1 program suite for a first round of screening (FIG. 4A). The small molecules were ranked according to their energy scores. The top 500 small molecules were then selected for a second round of screening by thermal shift binding assay using Mcl-1 protein and HR reporter assay (FIG. 4A). One lead compound (NSC320223, C23H18ClN3O3, MW: 419.86032) was identified as shown in FIGS. 4A and 4B, and was termed Mcl-1 inhibitor-223 (MI-223).

To confirm the binding of MI-223 with Mcl-1, isothermal titration calorimetry (ITC) was used to measure MI-223/Mcl-1 binding. ITC is a direct, label- and immobilization-free technique that measures the binding affinity between proteins and small-molecule ligands that interact with each other, and can analyze binding constant (KD) values in the millimolar and nanomolar range. ITC experiments were performed to assess MI-223/Mcl-1 binding using an auto-iTC200 instrument. Results revealed that MI-223 directly bound WT Mcl-1 protein with good binding affinity (KD value: 0.161±0.007 μM) (FIG. 4C, left panel). In contrast, MI-223 failed to bind to the BH1 deletion Mcl-1 mutant protein (ΔBH1) in ITC assay (FIG. 4C, right panel), suggesting that the BH1 domain is essential for Mcl-1 to interact with MI-223. In addition to the binding constant (KD) value measured by ITC, we also used fluorescence polarization (FP) to measure the inhibitory constant (KI) value using a fluorescence-labeled PUMA BH3 peptide. The PUMA BH3 peptide was chose for this FP assay to evaluate Mcl-1/MI-223 binding because it has been reported to bind specifically to the BH1 domain of Mcl-1. Results indicated that the KI value of MI-223/Mcl-1 binding in the FP assay was 0.193±0.0043 μM (FIG. 4D). Based on findings from both ITC (i.e., KD) and FP (i.e., KI), we conclude that MI-223 may directly bind to Mcl-1 with good affinity.

MI-223 not only disrupted the Mcl-1/Ku complex (FIG. 4E) but also potently inhibited HR activity in both H1299 and U2OS DR-GFP cells in a dose-dependent manner (FIG. 4F). To assess whether Mcl-1 is essential for the effect of MI-223 on HR activity, Mcl-1 was knocked out from H1299 cells using CRISPR/Cas9 to generate Mcl-1-deficient cells. WT Mcl-1, Ku binding-deficient mutant ΔBH1, and empty vector control were exogenously expressed in Mcl-1-knockout H1299 (Mcl1−/− H1299) cells, followed by treatment with MI-223 for 24 hours and analysis of HR efficacy. Results indicated that MI-223 induced a dose-dependent reduction of HR efficacy in H1299 parental cells, and knockout of endogenous Mcl-1 from H1299 cells resulted in a significant decrease in HR efficacy. MI-223 had no significant further effect on HR efficacy in Mcl-1-deficient H1299 cells. Intriguingly, expression of exogenous WT Mcl-1 but not the Ku binding-deficient ΔBH1 Mcl-1 mutant in Mcl-1-deficient H1299 cells restored the inhibitory effect of MI-223 on HR activity. These findings suggest that Mcl-1 expression is essential for the inhibitory effect of MI-223 on HR activity, which requires its BH1 domain.

To test whether inhibition of HR by MI-223 sensitizes cancer cells to DNA replication stress, H1299 cells were treated with olaparib or Hu in the absence or presence of MI-223, followed by analysis of Rad51 foci and clonogenic survival. Olaparib or Hu induced Rad51 foci and MI-223 strongly inhibited Rad51 foci formation (FIG. 4G), suggesting that MI-223 suppresses HR-dependent DNA repair. Importantly, MI-223 suppression of HR DNA repair activity synergizes with olaparib or Hu to kill H1299 lung cancer cells (FIG. 4H). Annexin V binding assays revealed that MI-223 did not induce significant apoptotic cell death, indicating that MI-223-induced cell killing occurs mainly through suppression of Mcl-1-enhanced HR DNA repair activity, which occurs independently of apoptosis.

Whether MI-223 and DNA replication stress agents synergistically inhibit cancer growth in vivo, nude mice with non-small cell lung carcinoma (i.e., H1299) xenografts were treated with MI-223 (40 mg/kg/d), olaparib (40 mg/kg/d), Hu (500 mg/kg), and the combination of MI-223 with olaparib or Hu for 3 weeks. Importantly, the combination of MI-223 with olaparib or Hu exhibited significantly greater efficacy than a single agent alone in suppressing lung tumor growth in vivo (FIGS. 5A and 5C) leading to sustained tumor repression. Compared with olaparib or Hu alone, there was significant reduction of Ki-67 in association with increased levels of γ-H2AX in tumor tissues from animals treated with the combination (FIGS. 5B and 5D), indicating that MI-223 blocks the HR-dependent repair of olaparib- or Hu-induced DNA damage, leading to increased cell killing in tumor tissue. There was no significant weight loss, increase in alanine transaminase, aspartate transaminase, or blood urea nitrogen, nor reduction in wbcs, rbcs, hemoglobin, or platelets, in mice treated with MI-223 alone or in combination with olaparib or Hu. Histopathologic evaluation of harvested normal tissues (brain, heart, lung, liver, spleen, kidney, and intestine) revealed no evidence of normal tissue toxicity.

What is claimed is:
1. A method of treating cancer comprising administering an effective amount of a compound 2-(2-chlorophenyl)-3-(((5-ethoxy-6-oxocyclohexa-2,4-dien-1-ylidene)methyl) amino)quinazolin-4(3H)-one or salt thereof to a subject in need thereof.
2. The method of claim 1, where the compound is administered in combination with hydroxyurea or olaparib.
3. The method of claim 1, where the compound is administered in combination with another anticancer agent.

4. The method of claim 1, wherein the compound is administered in combination with bevacizumab, trastuzumab, imatinib, lenalidomide, pemetrexed, bortezomib, cetuximab, leuprorelin, abiraterone, alemtuzumab, nivolumab, pembrolizumab, pidilizumab, atezolizumab, avelumab, cyclophosphamide, methotrexate, 5-fluorouracil, doxorubicin, mustine, vincristine, procarbazine, prednisolone, bleomycin, vinblastine, dacarbazine, etoposide, cisplatin, epirubicin, cisplatin, capecitabine, folinic acid, oxaliplatin, or combinations thereof.

5. The method of claim 4 wherein the compound is administered in combination with cyclophosphamide, methotrexate, and fluorouracil; doxorubicin, and cyclophosphamide; mustine, vincristine, procarbazine, and prednisolone; doxorubicin, bleomycin, vinblastine, and dacarbazine; cyclophosphamide, doxorubicin, vincristine, and prednisone;

rituximab cyclophosphamide, doxorubicin, vincristine, and prednisone; bleomycin, etoposide, and cisplatin; methotrexate, vinblastine, doxorubicin, and cisplatin; folinic acid, 5-fluorouracil, and oxaliplatin; cyclophosphamide, doxorubicin, and vincristine; or epirubicin, cisplatin, and 5-fluorouracil.

6. The method of claim 1, wherein the subject is a human diagnosed with cancer.

7. The method of claim 6, wherein the cancer is lung cancer, Hodgkin's or non-Hodgkin's lymphoma, chronic lymphoid leukemia, colorectal cancer, breast cancer, esophagus cancer, stomach cancer, leukemia, GI cancer, multiple myeloma, mantle cell lymphoma, colon cancer, brain cancer, head and neck cancer, prostate cancer, or ovarian cancer.

* * * * *